(12) United States Patent
Reecy et al.

(10) Patent No.: US 7,700,291 B2
(45) Date of Patent: Apr. 20, 2010

(54) GENETIC TEST FOR THE IDENTIFICATION OF DWARFISM IN CATTLE

(75) Inventors: James M. Reecy, Ames, IA (US); James E. Koltes, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 591 days.

(21) Appl. No.: 11/556,284

(22) Filed: Nov. 3, 2006

(65) Prior Publication Data

US 2007/0238110 A1    Oct. 11, 2007

Related U.S. Application Data

(60) Provisional application No. 60/733,219, filed on Nov. 3, 2005.

(51) Int. Cl.
C12Q 1/68 (2006.01)
C12P 19/34 (2006.01)

(52) U.S. Cl. .......................................... 435/6; 435/91.2

(58) Field of Classification Search ........................ None
See application file for complete search history.

(56) References Cited

OTHER PUBLICATIONS

Takeda et al. (PNAS, Aug. 2002, vol. 99, No. 16, pp. 10549-10544).*
Takami et al. 2002, Animal Genetics, 33, 351-355.*
Mishra et al. Animal Genetics, 2003, vol. 34, pp. 311-312.*
Andelfinger, G. et al., "Radiation hybrid mapping and genomic organization of canine TBX2 and TBX 4", 2003 International Society for Animal Genetics, Animal Genetics, 34, pp. 302-318.
Chikuda, Hirotaka et al., "Cyclic GMP-dependent protein kinase II is a molecular switch from proliferation to hypertrophic differentiation of chondrocytes" 2004 Genes & Development 18:2418-2429.
Davoli, R. et al., "Radiation hybrid mapping of three skeletal muscle genes (CLM, ECH1 and TNNT1) to porcine chromosome 6", 2003 International Society for Animal Genetics, Animal Genetics, 34, pp. 302-318.
Koltes, James E. et al., "Discovery of a putative causal mutation for Angus dwarfism" NC-1010 Meeting Plant and Animal Genome XIV, 2006, 11 pages.
Koltes, James E. et al., "Identification of a putative causal mutation for dwarfism in cGMP dependant, type II, protein kinase (PRKG2)" 2006, 1 page.
Pfeifer, Alexander et al., "Intestinal Secretory Defects and Dwarfism in MIce Lacking cGMP-Dependent Protein Kinase III", Science, Dec. 20, 1996, vol. 274, pp. 2082-2086.

* cited by examiner

Primary Examiner—Juliet C Switzer
(74) Attorney, Agent, or Firm—McKee, Voorhees & Sease, P.L.C.

(57) ABSTRACT

Genetic markers for identifying bovine carriers of dwarfism in cattle, particularly Angus cattle is described. The genetic markers, including the microsatellite markers BMS4311 and AFR227 and the bovine PRKG2, BMP2K, BMP3, FGF5 genes, are located on bovine chromosome BTA6. One SNP, a polymorphism is located in the protein kinase domain within exon 15 of the bovine PRKG2 gene and is identified as being causative and diagnostic for dwarfism.

5 Claims, 11 Drawing Sheets

Figure 1.

```
Bovine: 146  gtcattctcacctgcaaagcctccgaatcagatcctcaggtcgtcttgttatctttctgg  205
             |||||||||||||||||||||||||||||| |||||||||||| |||||||| ||||
Human:  210  gtcattctcacctgcaaagcctccgaatcaaatcctcaggtcgtcgtgttatcttcctgg  151

Bovine: 206  gaaaatccattttttcaatgcctttgagaatcagattgtaggtcatcatttggtcaatcc  265
             |||||||||||||||||||||| ||||||||||| |||||||||||||||||||||| ||
Human:  150  gaaaatccattttttcaattcctttgagaatcaaattgtaggtcatcatttggtcaaccc  91

Bovine: 266  cagaaaaaggagggctaga  284
             ||||||| || |||||||||
Human:  90   cagaaaagggtgggctaga  72
```

Figure 2.
3'-
*TGGGAAGCCCAAAGTAGAAATGATTTTCTTTAAATATACTCTAACTACATAGAAAAGTACT
ATAAGTAAATACACATATAACTTTAAAATGGCAGCAGAAATAAGAAGCCTTCACACTTT/G
CCCTAAAAACAAAGGATTTTTAATAGTCATTCTCACCTGCAAAGCCTCCGAATCAGATCCT
CAGGTCG/ATCTTGTTATCTTTCTGGGAAAATCCATTTTTTCAATGCCTTTGAGAATCAGA
TTGTAGGTCATCATTTGGTCAATCCCAGAAAAGGAGGGCTAGAGAAAAGCCAA/TAATAG
GACATTAGGACCCACATCTGAGACACATTTACAGCTGATATTCCATCCTCCCTCTTTCCCT
CCTA     -5'*

Figure 3

5' Untranslated region

Not Available

Exon 1 (and flanking intron)
*CACTAGGTAACCTCCGATTCTGTGCCTTCTCTCAGG*TCCTTGAGCAAAATGGGAAATGGTT
CGGTGAAACCCAAACACTCCAAGAATCCAGATGGGCACCCCGGGAACCTCACCGCCAGCGC
CCTCCGGAGCAGGGTGACAGAGCTGGAAAGAGAGCTGAGAAGGAAGGATGCTGAGATCCAG
GAGCGGGAATACCACCTGAAGGAGCTGCGGGAGCAGCTGTCCAAACAGACTGTGGCCATCG
CGGAGCTCACGGAGGAGCTCCAGAACAAGTGCATCCAGCTGAACAAGCTTCAGGATGTGGT
GCACCTGCAGGGAGGAAGCCTGCCCCGGGCGTCCCCGGACAAAGTGCCTCTTGAGGTTCAG
CGGAAGACCTCGGGATTGGTCTCCCTCCACAGCAGGAGGGGAGCGAAGGCTGGAGTGTCCG
CCGAGCCGACCACCCGAACCTATGACCTCAACAAACCCCCTGAATTTTCCTTTGAGAAAGC
AAGAGTCAGAAAGGACTCCAGGTAAGACGTTCCCCCAGCTTTTTGGCTCC/TATGGCATTC
ACATGATGAAACGTTAA/GAGTGCTATTTACTGAGTCTCCTCAGTGGACAAGAGTGTATGA
ACCTTTTCAGATTTTGGATAGAGGGGCTGAGGAA

Exon2 (and flanking intron)*no SNPs!***
*TCCATGAGTCAGCTCTTCACATCAGG*TGGCCAAAGTATTGGTGCTTCAGCTTCAGCATCAG
TCCTTCCAATGAATATTCAGGGTTGAAATCCTTTAGGATTGACTGGTTAAAGTTGTAAACA
CATGGGTAGTAATATTAAGAATAAAGATGTTTTTCACTAATTGTAACTCAACATTTCCTTT
CCATTACATCAGTGAGAAGAAGCTCATTACAGATGCCCTTAATAAAAATCAATTTCTGAAG
AGACTGGATCCTCAGCAGATCAAAGACATGGTGGAATGCATGTATGGGAGAAACTACCAGC AAGGGAGCTACATTATTAAGCAAGGAGAACCAGGAAACCATATCTTTGTACTGGCAG*GTGG*
*GTTTCACAGATTTTTACAGTTATCATATAACAAATATTTGCCTATTGTTTAATGATTTTTT*
*GCACATATTTATAAAAATGCAAAATTGGTTGTTCTATTTGTAGAAAATATAACAGATTGAG*
*TTCATGAAATAATAATATTTGTTGGTCGAATCATCCTGATGTTAATAACTAATATTTATAG*
*AATGCTTTCTATATGTCC*

Exon 3 (and flanking intron)
*CATTCCTAACCACTTTATTACAATGAA/GATCGTAAGATATCTCACCTAGATGCTTTGT*
*G/ATACCTGCTGCTTGTTTTCTTTTAATTTATGGAATCTCGATGGATTTTGCTTATTTGTG*
*TGTTCTTGCATTCTACTTGATAGAGGGTCGACTAGAGGTGTCCCAAGGGGAGAAATTGCTG*
TCATCCATCCCTATGTGGACCACGTTTGGGGAGCTAGCCATTTTATACAACTGTACAAGAA
CTGCCTCTGTGAAAGGTAACAGAAGAAGAAATGCTCTAGTTTTCAATTGCTACACAGTGTT

Exon 4 (and flanking intron)
CCATCAACACG/AAAGGGCAAAATTAGCAAGAGAAATAAAT/CCAGTGAAAAGGCTAAT
G/AGGAATGAAACACAAATTTTCATAGATAGTGGCACTTACTGCAAGAAAATACTTGTGTT
*CCTTTGGCTTAGTCATGTGGAAATGCTTAAATAAGAAAAGCTATAGTAAAATAATTACTC*
*TGATAAAACCAACATACCCACAGTATGGCTAGACCAGCTTCTCCTTCTGCCATCAATGTGT*
*TACTCTTACCTTCTGAGGAAGTTTCTGTACTGTTCATCTCTAGCTTGAGCTGTCCTTCTCA*
*TTATATTCTGGAATACCTCTCGATCTAGTGCCCATGTTTTAACATTGGTAATAGCTTTAGA*
*AAAATCAAGAAAATAATAAAACTCTGTTGAGCTCTTATATTAAGAAAACATTCCAAAATGT*
*TAATCAATCAATTTTTCATGTACTGTCATAAAATTATCTTTCTTGGAAAACGCATTATTTA*
*AACACGCAAAATGGAAGGAAGTAGTGATGTAAGAGTAGGTAATTTTATAAAATCATTTTT*
*GGCTTTGAAATGAACCATGATTTGGAAGTGAGCAG*

Exon 5 (and flanking intron)
*GTCTGCCTGTTTTATGTGATCGTATAATTTCAGTGTATTTACAATATGATTTTGAAATTC/*
*TAGTTATG/TTATG :/TAT :/GATATAT ::/AT*GGAGGTTTACTTTGGAAAAATTAAA
ATATT/CTGTGTAAATGCATGTATAAATCTATGTAGAGGTGTATATTTGTAGTTTAATTCA
GGAAGATAATTAAATAAAGGTTTCTTTTTAATTTTGAAGTGTATCCTTGCTGAAGAATTTA
CCTGAAGATAAACTAACCAAGATCATTGACTGCTTGGAAGTGG*TAAGAAATTTTAAAGTAA*
*AAAAAATATATTTCATTAAAAGATTGTATAATCTCATCATTATTAACCTTGTAAATGAATA*
*AAAAGGAAAAGATGGTGATTACTGGTCTACAGAAACCAGGAAACGTTTTCACAGTAGAAAA*
*ACTTTAGGCTAACTCACACTGAATTAAGGGCCTCG/A ATTGGGATTCA*

Exon 6 (and flanking intron)
*TATCCCCTTCCCCCTCCTCCAACCCTCACTTCCCCAGGTGTCTTCTGAGCAGAAGCTCCGT*
TACCTGCTCAACGCAGACAGACAACTTAGGCTGCAATGCACAACACTGCTGCTTTTATGGC
AAACAGATTTGAAATGCTTCTTTAGATTTACATTAAGCAAGCTTTCATTAATATTTAC
CTTTCCTTTTGCTAAAATGAAAAACGTACTTCCTTCCTCGCCCTCTCTAATAATGTAATCT
CCTTTGTCATAGTATTCC*TATTGGGATGAAAGAAAAAGAAAAGGTTAGATGCAGCAGAGAT*
*ATACAGATGAAGC/ACATAAATGAGACGAACATTCCATACCCA C/T TTCTGCTATTTTT*
*TGCTTACTGTAACTGTGATCTTCTTAAATATTGTAGTCAAAAGCCATGGAAAAGTAAGAAG*
*ACTTTTGCTTGTTTAC/TCTGAATTTATGTTTATCTTTCACATACACACAAAAAATATTCA*
*CCTGGAATA C/T TGTCAGGCATGGACACAGAAGACATGAAGAGAAA*

Exon 7 (and flanking intron)
Not available

**Exon 8 (and flanking intron)\*\*\*NO SNP\*\*\*\***
*GCCACAGACAGATTCAGATCAGAAGGCCTGGTTCCTTCCCATGAATTTTAATAGAATGTCC*
*TCGCAGCTGAGGATTGGCCAGCGTTTCCAAATGGTGATGAATGGGAAGACAGATGGGCCCT*
*TGGAGTAACAGAAGGCCGAGTCTTCAAAGGTGGCAATTGCTGGCATTCTCTAACATCAGTA*
*TACTCACTCTCGATCTATAACCAGGCATGCGACATCATTTTCCTCGGCGATAATGTTAGCT*
GATCTGACATCTTCACTGCAGACAAAAACAGGAAAAGTCAATTTTCTAGTGAGAAATTAGA CATCTATTTTTATTAGCGAATCTGCGACTGATATGAAACACCATCACTTAAACCTTCCAAA
GATGATGTGTTTCTGTAACATCATAATTTACACTCCACCCCTTCCC

Exon 9 (and flanking intron)
TTTGTGGAAGAATAATTTAAAACAACTCCCCCAAATTTTCTAGTGACAACACACTAGAAGT
TACCAATCACACCCTTCAGTTCCCTTCTTCATCAACTGCCAGAGTCACA*T/G*CCAGCTTAG
AAAAACATCTCCACTTACTTCGCATGTCTTTTTTCATCATCCCGGTTCAGGTTTGCCACAT
ACCCTTCAAGATATTTCTGGAGTTCTTCAAAAGTCCCCACTGTTTGGTTGAATGTTCTAAA
TGAATGAAATGAATAAAACAAAATAAAAAGCTCAGGGCTGACGGTTAACCACTGCAACTTG
CCATTCTTCTTCAGCTGATGAAAGCCTATTTGTATGGTTACTGAAAACTTTGCAAACTATT
TTTCAATAACTTATTTACATTCAGTTGCCATCAC

Exon 10 (and flanking intron)
AGCACACACCCACTATTATAAAATAGAGTGAAAACTGTACTCTCAATTATAGTCCAAAGTA
ACGTTTGGATAGCAATAACAATGCG*A/T*ATATTCCTCCAAGATACACTGGAATACAAAACA
AAACAAAAGTCAAAAGGCTTCTCTCAGATGCTTGAAACGTAAACCCCTTACAAGCTCAACT
CTTCCGAACCCACCAACGCCCAGTGTTGCGATAATCTCAAGGTTCTGGAAGGGGATGATG
AGGAAAATCTGGCCACTTTCTCCTTCAGTTGAATCATCTCCAAAGAGAGTGCTTTGGACAG
CTTCCAGCTAGACATGGATCTCCTGTACGAGAAAAGCGAAACTTTACATACGCTCCCTTAG
GCAAAGCAGGGGTCACAGCACACATAAATCCCACCCTTACATCAGTCTTATTTCTGCCAGT
AATTACTGCCCATAGTTGCCATAGAGTTTATCTCAACTTTTATAGAATCAGATTCAGTTAC
ATCTGGGG

Exon 11 (and flanking intron)
TAGAAGCACTCCAAAGAAGAACCTAAGATGCTAAAATTCTGGGAGCGAAACGCT*C/A*ACTT
ACTTCACAATGAAGGGTGAGCATAGCTCTTCCAGGATCTTCTTTTCTGAGTAGACATGCTC
CTGCTGCTTCGTGTCAACGATGTGCTTCTTCCTTATACACTTCATAGCAAAAGCAACGTTC
TCATTTTTCACCTTAACCTAGAGGAGAAGAGAACGAGCCCTCAAAATGAACTTACTAGGAA
AGATCTGCAATATCTATGTAAAACATGTGAACCAGCAGGAGTTCAAATCCTTTCACAGCTA
AATAGCATGGAAGCTTTTCACCACTTTAATCCCTCT

**Exon 12 (and flanking intron)\*\*\*NO SNP\*\*\***
TGAGCATCCAGTGT*C/T*TTTGTCAGATGTTTGGAAGGAGATGAGGACCATCCTTCAAAAAG
TTATTGGATGATGCTTTTAAGCAAACTTGAAGATGTTTTAGAACGGGATTTCTAATAATAA
TCGTGTTTTTCTTTTATTTTCACAGATTATATCGCACCTTCAAGGACAATAAGTATGTATA
CATGCTTCTGGAGGCCTGCTTAGGTGGGGAGCTGTGGAGTATATTAAGAGACAGGTAATGA
AAAAGAATTATATGCAATAACTTTTGTCTGTTCCTGCCTGGCCTAAAGGATGCTGTATTCA
TGACTATTTAAAGAAACATGAAGAAAGTCACTAAGAAATGAGTCTAAGGGACTTCCTTGCC
TCTCCAGTGGTTAAGACTTTGCCTTCTAATGCAGGAGGCACAGGTTCAATC

**Exon 13 (and flanking intron)\*\*\*NO SNP\*\*\***
CTAAATTTCTTTATGATCTGATTCATTGATGCTATGAAGTACTTTTTAGTGCTAATGCCTT
ATAAAGCATTTATATTGCATAAATATATAATATTATAATTGACACCTAGAATCTGCAACCA
GGATGTCTAGAGTTTTAAGAAGGAAAATGGTTTCGTTGCAGAGGCAGCTTTGATGAACCCA
CCTCCAAGTTCTGTGTTGCCTGTGTGACAGAAGCATTCGATTACCTGCATCGACTAGGTAT
TATCTACAGAGACCTGAAACCAGAAAACTTAATTCTAGATGCTGAGGGCTATCTTAAATTG
GTAAGACAAATTCTTATCCTGTGAGATATTTCTAAACATAAAGTTGTGCTGTAGTTGCAAT
TCTTTTTTTTTAAAAACTTTTATTTTAAATTAAAAAAATGTTTATGTTTAATTGGTGGGTA
ATTGTTTACAATGTTTTGTTGGTTTCTGCCATACAACACTGTGAATCAGTCATAAGTATAC
ATATATTCCCTCCCTCTAGAGTCACTCTCTCA

Exon 14 (and flanking intron)
GAAACCCCTTACGAAGTTAAACGGAGATTTAAAGAAGAGTGTGAGTTTTAC*A/G*ATCTCTG
AAGATTTCTTTGATCTTCTTTTCTAGGTTGACTTTGGATTTGCTAAGAAAATAGGATCTGG
ACAGAAAACATGGACGTTCTGTGGAACTCCAGAGTATGTAGCTCCTGAAGTCATTCTCAAC AAAGGACATGACTTCAGTGTGGATTTTTGGTCCCTGGGAATTCTAGTATATGAGCTCCTCA
CGGGCA*GTAAGTACCTTCAAGTTGTGTTCA:/GCCTCTTCTTCAGAGAACTGCAAAAATA
ACTTACTCATGATAAT(ACAT/::::)AC(ATATATATATATATATATATATAT/::::::
:::::::::::::::::::)ATATATATATATATGTATATAAGAATTTAACATTTTGGAAGT
GTTTTTGATTAAGCATGATGCCTTTTCCTCTTC*

Exon 15 (and flanking intron)
*TGGGAAGCCCAAAGTAGAAATGATTTTCTTTAAATATACTCTAACTACATAGAAAAGTACT
ATAAGTAAATACACATATAACTTTAAAATGGCAGCAGAAATAAGAAGCCTTCACACTTT/G
CCCTAAAAACAAAGGATTTTTAATAGTCATTCTCACCTGCAAAGCCTCCGAATCAGATCCT
CAGGTCG/ATCTTGTTATCTTTCTGGGAAAATCCATTTTTTCAATGCCTTTGAGAATCAGA
TTGTAGGTCATCATTTGGTCAATCCCAGAAAAGGAGGGCTAGAGAAAAGCCAA/TAATAG
GACATTAGGACCCACATCTGAGACACATTTACAGCTGATATTCCATCCTCCCTCTTTCCCT
CCTA*

Exon 16 (and flanking intron)
*AAGTTTCAAGATGACCACATTTTAAAAATATTTCTATATTTTCTGGGCAGAGAAATATGTA
CCTGTGTTTCTTAATGTCATTGATTCCATTCTTCAGATTTCCCAGTCTTTCTGTTGGATTT
TGCCTACAAAAAGAGTTTTCAATCAGCTCATAATAATTATGCTTGAGTGAATTTTACATTC
AAATTTTATGCTTTTTCTTTATCCATTCATTGATTTTGTCAGTAATATGTATG/AAACCAG
GCACATTTGTGTACAGGGAGACAGAAAACATATGCCCTCTCTGGAGGAGCCACAGTCCAAT
TACAGTCAGAAATAT*

Exon 17 (and flanking intron)
*TAACTTAAATTTAAAAACTTAAAAT/ATTTTAAGATCTATTATATACATAC/TACTTGAGT
TTGCACACATGATCACACACTTAAACTCTGTTTACAAAAACACCTAGAAAAAAATCAAGAG
AGTAATATCAGCTACCATACCTCTCTTTGTAAAGGTGATGGAAGATTTCGTGCTTTCAGTC
CCTCCCAATTAAAACCATTTAACCACCTGAGAAATGAGAAAAGCACAGAGGAATATTACTG
ATCTGATACACTATTAGCATGTCATGTTATCTGTCAACCCATTCTGTTGCCTGCTTCCTGC
CTGG/CCAATGGTGTAGCTGTAAGTAATCAGAG/AAGAAATACTCACTGTGCCCACAA/CAC
ACACACACACACACACGTGTGTATCTCACATTAAATCCATGCCCACTACTTTCCCGGGA
GGGGGCTTTAGTGTCTCCAGCAGTCAGTCTAGGTCTCCCT*

Exon 18 (and flanking intron)
**\*\*Definition of exon, intron boundaries is not clear in this
exon. (See alignment below in appendix I)**

ACAGATCACAGCTACTTTGACAAGTATCCTCCTGAAAGGGGGTGCCTCCAGATGAGCTGT
CAGGCTGGGACAAAGACTTCTGAGAGAAGGGAAGACGATCACTGCCTACAGAATCAAGAGG
ACTAGAA/CGTCCTAGTAATCCAACACTGATCATTTCTC/ATTTGGAGTTTGACACTATCT
TTTGGAAGACCATTAGAGAAACGAATCCCTGCCCATGATCTGG:/CGGGGA/TGGGGG**::/
GGTGGG/T**CGAGAGTGGGTGCAGAGGTGGTTTTGAATTATAACGTCTCATTTAGATGCTGT
GAATTATTCATGTGTTCCATTCTTTGCTTTTCTCAAATGTTGAAGGCTGTCTTAGTCCCCT
CTTCAAAGTCAGAACCATTTTTGT/GTAAAGGGACATTATCTTCTCTGCAATCTATTGCTC
CGTCCTTATCATTCTTGTCTTGTTTAAGTCCTAGTAAGGTATAAAAAATGTCTTGTCCTTG
AGCAACTAAGTCATTCAAATAGAAGGAAGAACAAGGGTTAATTTTGGAAAT/ATTTCCCTT
TCCCAACAATCTCACGTAAGCATCAC/TGGCATCTTGAAATTGCGGTTTGCAGGAAACTTG
TTAGTCAATAGAAATTCTTGATTTTTACCTGCATTCAACCTAGAAATAAATTAATATGCTT
CTGAAAGTAGCCTGGGGAAAGGCAAATTTGAATATTAGTCCTTGGTACCACTTCCTAACAT
AAATGAGTTAATTCTTCCTTCCAGGGAATTATATTG/ATATTGGAGAACTTAGAAAAAATA
AACAAAGCAAAAATATTTTTTATTTTCCCG/ATGACCAGCTGTGGGACCTCAGAGACTTT
GCAA/GAAGTCTTGTGAGAGGTGGTTGTAACGTGTGGTTAATTGAGGGGCCTTTGGAAAAG
TTTTATCTTACATATTAAATATTTTCACG/AATCAACTTAGAAAATATGCAGAAACTAGAT
TGTGAAGGCTTTTACTTCCCCTTACCTGTGGAGGAGAAAAACTTCCAAAAGGTCAAAATGT
TGACTCTTTGAGACTCTGAGATATTTTGGCCAGTTCTGTGACTGTTGCTATTAATAAACCA

AGAGTATAGAATAAACACAGTTAATTTTTAATGAAAATCCCATTGGCAAATATTGATGCAA
ACCAAAATCACTGTTGCATTAATAATTTTTTAAAAAGATGTATGAGTCATGGGACTATTTA
TAATTTTAGATATGTAAGGCAGGCCAGCCGCTCGAGAAGTAATGCCCAGTAACAAGGACAC
CCGACATCAA

**3' Untranslated region   \*\*\*NO SNP\*\*\***
*TGCTTTCTGAAGTGTTAAAACAGATGAGTGAGGCCCCACCCAAGAAGGTGCATCCTTAACA*
*AATTATATTTCCACATTTAGAATCTTTTTGCTGAACCAAAGAATTTTTGTTTCCTGGAGTA*
*GTATTTTTAAAGTTGTACATAGATGAAGCATTTTTAATAGGATCGACGTAACCCGCTTAAT*
*GAATTTCTAAGATTTTTTAAAGAGTTTTATTTGCATTTGGTTTGTAAGCACTGTATGTTTT*
*TCCATGTATATATTTTTCAATTACCCACCTATAAATGTAGGAAATTTATGTATTAGGTTAA*
*TATTAGAACTGTACAGTTATACTAGCAATGGTATTCTCAAAGGTGATCAGTAGTTGTAATT*
*CAAAAACAGCTTACAAATATACAAATAAAAACCAACTTAGAGTACTACAAGTTTACTTTGG*
*CTATGACTGGCCATGCCATTATATAATCTCCACATGTGGTTTTATTGGGTTTCCTTTAGAG*
*TACTTTATAAAGATGCAGAAATGAGAGACCTAACCATAATATAAACCCAATTCTATTCTGT*
*AGCTGGATGACCTTGGGAAAATGACTTCACTTTTTTGAGTACTAGCTTTCTCACCTGTAGA*
*AAAAGGCACACTAAAATAATACCTACATTA*

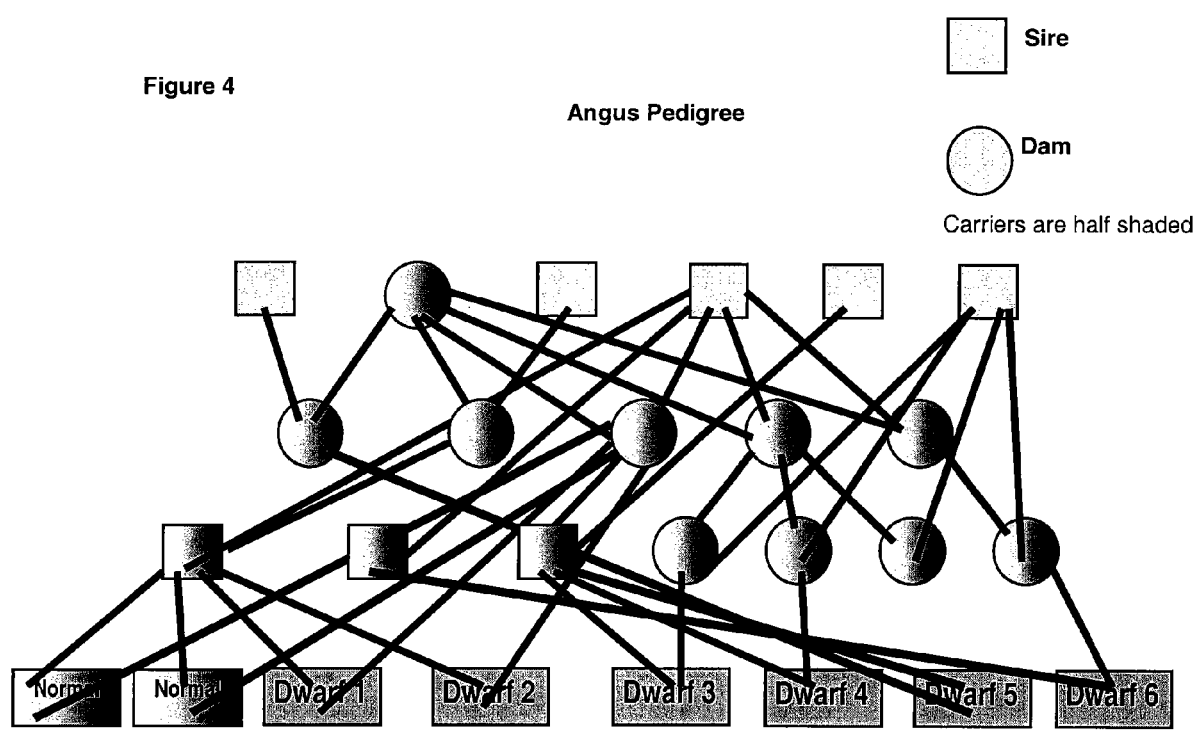

SEQUENCE LISTING

<160> NUMBER OF SEQ ID NOS: 26

<210> SEQ ID NO 1
<211> LENGTH: 139
<212> TYPE: DNA
<213> ORGANISM: Bos taurus

<400> SEQUENCE: 1

| gtcattctca | cctgcaaagc | ctccgaatca | gatcctcagg | tcgtcttgtt | atctttctgg | 60 |
| gaaaatccat | tttttcaatg | cctttgagaa | tcagattgta | ggtcatcatt | tggtcaatcc | 120 |
| cagaaaaagg | agggctaga | | | | | 139 |

<210> SEQ ID NO 2
<211> LENGTH: 139
<212> TYPE: DNA
<213> ORGANISM: Homo sapiens

<400> SEQUENCE: 2

| gtcattctca | cctgcaaagc | ctccgaatca | aatcctcagg | tcgtcgtgtt | atcttcctgg | 60 |
| gaaaatccat | tttttcaatt | cctttgagaa | tcaaattgta | ggtcatcatt | tggtcaaccc | 120 |
| cagaaaaggg | tgggctaga | | | | | 139 |

<210> SEQ ID NO 3
<211> LENGTH: 364
<212> TYPE: DNA
<213> ORGANISM: Bos sp.

<400> SEQUENCE: 3

| atcctcccttt | tctccctcct | accttatagt | cgacatttac | acagagtcta | cacccaggat | 60 |
| tacaggataa | waccgaaaag | agatcgggag | gaaaagacc | ctaactggtt | tactactgga | 120 |
| tgttagacta | agagtttccg | taacttttt | acctaaaagg | gtctttctat | tgttctrctg | 180 |
| gactcctaga | ctaagcctcc | gaaacgtcca | ctcttactga | taattttag | gaaacaaaaa | 240 |
| tcccktttcac | acttccgaag | aataaagacg | acggtaaaat | ttcaatatac | acataaatga | 300 |
| atatcatgaa | aagatacatc | aatctcatat | aaatttcttt | tagtaaagat | gaaacccgaa | 360 |
| gggt | | | | | | 364 |

<210> SEQ ID NO 4
<211> LENGTH: 640
<212> TYPE: DNA
<213> ORGANISM: Bos sp.

<400> SEQUENCE: 4

| cactaggtaa | cctccgattc | tgtgccttct | ctcaggtcct | tgagcaaaat | gggaaatggt | 60 |
| tcggtgaaac | ccaaacactc | caagaatcca | gatgggcacc | ccgggaacct | caccgccagc | 120 |
| gccctccgga | gcagggtgac | agagctggaa | agagagctga | gaaggaagga | tgctgagatc | 180 |
| caggagcggg | aataccacct | gaaggagctg | cgggagcagc | tgtccaaaca | gactgtggcc | 240 |
| atcgcggagc | tcacggagga | gctccagaac | aagtgcatcc | agctgaacaa | gcttcaggat | 300 |
| gtggtgcacc | tgcagggagg | aagcctgccc | cgggcgtccc | cggacaaagt | gcctcttgag | 360 |
| gttcagcgga | agacctcggg | attggtctcc | ctccacagca | ggaggggagc | gaaggctgga | 420 |
| gtgtccgccg | agccgaccac | ccgaacctat | gacctcaaca | aaccccctga | attttccttt | 480 |
| gagaaagcaa | gagtcagaaa | ggactccagg | taagacgttc | ccccagcttt | ttggctcyat | 540 |
| ggcattcaca | tgatgaaacg | ttaragtgct | atttactgag | tctcctcagt | ggacaagagt | 600 |
| gtatgaacct | tttcagattt | tggatagagg | ggctgaggaa | | | 640 |

<210> SEQ ID NO 5
<211> LENGTH: 567
<212> TYPE: DNA
<213> ORGANISM: Bos sp.

<400> SEQUENCE: 5

```
tccatgagtc agctcttcac atcaggtggc caaagtattg gtgcttcagc ttcagcatca      60
gtccttccaa tgaatattca gggttgaaat cctttaggat tgactggtta aagttgtaaa     120
cacatgggta gtaatattaa gaataaagat gttttttcact aattgtaact caacatttcc    180
tttccattac atcagtgaga agaagctcat tacagatgcc cttaataaaa atcaatttct     240
gaagagactg atcctcagc agatcaaaga catggtggaa tgcatgtatg ggagaaacta      300
ccagcaaggg agctacatta ttaagcaagg agaaccagga accatatct tgtactggc       360
aggtgggttt cacagatttt tacagttatc atataacaaa tatttgccta ttgtttaatg    420
atttttttgca catatttata aaaatgcaaa attggttgtt ctatttgtag aaaatataac    480
agattgagtt catgaaataa taatatttgt tggtcgaatc atcctgatgt taataactaa    540
tatttataga atgctttcta tatgtcc                                         567
```

<210> SEQ ID NO 6
<211> LENGTH: 299
<212> TYPE: DNA
<213> ORGANISM: Bos sp.

<400> SEQUENCE: 6

```
cattcctaac cactttatta caatgaratc gtaagatatc tcacctagat gctttgtrta     60
cctgctgctt gttttctttt aatttatgga atctcgatgg attttgctta tttgtgtgtt   120
cttgcattct acttgataga gggtcgacta gaggtgtccc aaggggagaa attgctgtca    180
tccatcccta tgtggaccac gtttggggag ctagccattt tatacaactg tacaagaact    240
gcctctgtga aggtaacag aagaagaaat gctctagttt tcaattgcta cacagtgtt     299
```

<210> SEQ ID NO 7
<211> LENGTH: 576
<212> TYPE: DNA
<213> ORGANISM: Bos sp.

<400> SEQUENCE: 7

```
ccatcaacac raagggcaaa attagcaaga gaaataaayc agtgaaaagg ctaatrggaa     60
tgaaacacaa attttcatag atagtggcac ttactgcaag aaaatacttg tgttcctttg   120
gcttagtcat gtggaaaatg cttaaataag aaaagctata gtaaaataat tactctgata  180
aaaccaacat acccacagta tggctagacc agcttctcct tctgccatca atgtgttact    240
cttaccttct gaggaagttt ctgtactgtt catctctagc ttgagctgtc cttctcatta   300
tattctggaa tacctctcga tctagtgccc atgttttaac attggtaata gctttagaaa    360
aatcaagaaa ataataaaac tctgttgagc tcttatatta agaaaacatt ccaaaatgtt    420
aatcaatcaa tttttcatgt actgtcataa aattatcttt cttggaaaac gcattattta    480
aacacgcaaa atggaaggaa gtagtgatgt aaagagtagg taattttata aaatcatttt    540
tggctttgaa atgaaccatg atttggaagt gagcag                              576
```

<210> SEQ ID NO 8
<211> LENGTH: 457
<212> TYPE: DNA
<213> ORGANISM: Bos sp.

<400> SEQUENCE: 8

```
gtctgcctgt tttatgtgat cgtataattt cagtgtattt acaatatgat tttgaaatty     60
```

| | |
|---|---:|
| agttatktat gtatgatata tatggaggtt tactttggaa aaattaaaat atytgtgtaa | 120 |
| atgcatgtat aaatctatgt agaggtgtat atttgtagtt taattcagga agataattaa | 180 |
| ataaaggttt cttttttaatt ttgaagtgta tccttgctga agaatttacc tgaagataaa | 240 |
| ctaaccaaga tcattgactg cttggaagtg gtaagaaatt ttaaagtaaa aaaaatatat | 300 |
| ttcattaaaa gattgtataa tctcatcatt attaaccttg taaatgaata aaaggaaaa | 360 |
| gatggtgatt actggtctac agaaaccagg aaacgttttc acagtagaaa aactttaggc | 420 |
| taactcacac tgaattaagg gcctcrattg ggattca | 457 |

<210> SEQ ID NO 9
<211> LENGTH: 521
<212> TYPE: DNA
<213> ORGANISM: Bos sp.

<400> SEQUENCE: 9

| | |
|---|---:|
| tatccccttc ccctcctcc aaccctcact tccccaggtg tcttctgagc agaagctccg | 60 |
| ttacctgctc aacgcagaca gacaacttag gctgcaatgc acaacactgc tgcttttatg | 120 |
| gcaaacagat ttgaaatgct tctttagatt tacattaagc aagctttcat taatatttac | 180 |
| ctttcctttt gctaaaatga aaacgtact tccttcctcg ccctctctaa taatgtaatc | 240 |
| tcctttgtca tagtattcct attgggatga aagaaaaaga aaaggttaga tgcagcagag | 300 |
| atatacagat gaagmcataa atgagacgaa cattccatac ccayttctgc tattttttgc | 360 |
| ttactgtaac tgtgatcttc ttaaatattg tagtcaaaag ccatggaaaa gtaagaagac | 420 |
| ttttgcttgt ttayctgaat ttatgtttat ctttcacata cacacaaaaa atattcacct | 480 |
| ggaataytgt caggcatgga cacagaagac atgaagagaa a | 521 |

<210> SEQ ID NO 10
<211> LENGTH: 412
<212> TYPE: DNA
<213> ORGANISM: Bos sp.

<400> SEQUENCE: 10

| | |
|---|---:|
| gccacagaca gattcagatc agaaggcctg gttccttccc atgaattta atagaatgtc | 60 |
| ctcgcagctg aggattggcc agcgtttcca aatggtgatg aatgggaaga cagatgggcc | 120 |
| cttggagtaa cagaaggccg agtcttcaaa ggtggcaatt gctggcattc tctaacatca | 180 |
| gtatactcac tctcgatcta taaccaggca tgcgacatca tttttcctcgg cgataatgtt | 240 |
| agctgatctg acatcttcac tgcagacaaa acaggaaaa gtcaattttc tagtgagaaa | 300 |
| ttagacatct attttttatta gcgaatctgc gactgatatg aaacaccatc acttaaacct | 360 |
| tccaaagatg atgtgtttct gtaacatcat aatttacact ccaccccttc cc | 412 |

<210> SEQ ID NO 11
<211> LENGTH: 398
<212> TYPE: DNA
<213> ORGANISM: Bos sp.

<400> SEQUENCE: 11

| | |
|---|---:|
| tttgtggaag aataatttaa aacaactccc ccaaattttc tagtgacaac acactagaag | 60 |
| ttaccaatca caccctttcag ttcccttctt catcaactgc cagagtcaca kccagcttag | 120 |
| aaaaacatct ccacttactt cgcatgtctt ttttcatcat cccggttcag gtttgccaca | 180 |
| tacccttcaa gatatttctg gagttcttca aaagtcccca ctgtttggtt gaatgttcta | 240 |
| aatgaatgaa atgaataaaa caaaataaaa agctcagggc tgacggttaa ccactgcaac | 300 |

```
ttgccattct tcttcagctg atgaaagcct atttgtatgg ttactgaaaa ctttgcaaac    360 tattttcaa taacttattt acattcagtt gccatcac                              398

<210> SEQ ID NO 12
<211> LENGTH: 494
<212> TYPE: DNA
<213> ORGANISM: Bos sp.

<400> SEQUENCE: 12
agcacacacc cactattata aaatagagtg aaaactgtac tctcaattat agtccaaagt     60
aacgtttgga tagcaataac aatgcgwata ttcctccaag atacactgga atacaaaaca   120
aaacaaaagt caaaaggctt ctctcagatg cttgaaacgt aaaccccta caagctcaac    180 tcttccgaac ccaccaacgc ccagtgttgc gataatctca aggttctgga aggggatga    240 tgaggaaaat ctggccactt tctccttcag ttgaatcatc tccaaagaga gtgctttgga   300
cagcttccag ctagacatgg atctcctgta cgagaaaagc gaaactttac atacgctccc   360
ttaggcaaag caggggtcac agcacacata atcccaccc ttacatcagt cttatttctg    420
ccagtaatta ctgcccatag ttgccataga gtttatctca acttttatag aatcagattc   480
agttacatct gggg                                                      494

<210> SEQ ID NO 13
<211> LENGTH: 339
<212> TYPE: DNA
<213> ORGANISM: Bos sp.

<400> SEQUENCE: 13
tagaagcact ccaaagaaga acctaagatg ctaaaattct gggagcgaaa cgctmactta     60
cttcacaatg aagggtgagc atagctcttc caggatcttc ttttctgagt agacatgctc   120
ctgctgcttc gtgtcaacga tgtgcttctt ccttatacac ttcatagcaa aagcaacgtt   180
ctcatttttc accttaacct agaggagaag agaacgagcc ctcaaaatga acttactagg   240
aaagatctgc aatatctatg taaaacatgt gaaccagcag gagttcaaat cctttcacag   300
ctaaatagca tggaagcttt tcaccacttt aatccctct                           339

<210> SEQ ID NO 14
<211> LENGTH: 415
<212> TYPE: DNA
<213> ORGANISM: Bos sp.

<400> SEQUENCE: 14
tgagcatcca gtgtytttgt cagatgtttg gaaggagatg aggaccatcc ttcaaaaagt     60
tattggatga tgcttttaag caaacttgaa gatgttttag aacgggatttt ctaataataa  120 tcgtgttttt cttttatttt cacagattat atcgcacctt caaggacaat aagtatgtat   180
acatgcttct ggaggcctgc ttaggtgggg agctgtggag tatattaaga gacaggtaat   240 gaaaagaat tatatgcaat aacttttgtc tgttcctgcc tggcctaaag gatgctgtat    300
tcatgactat ttaaagaaac atgaagaaag tcactaagaa atgagtctaa gggacttcct   360
tgcctctcca gtggttaaga ctttgccttc taatgcagga ggcacaggtt caatc         415

<210> SEQ ID NO 15
<211> LENGTH: 520
<212> TYPE: DNA
<213> ORGANISM: Bos sp.
```

<400> SEQUENCE: 15

```
ctaaatttct ttatgatctg attcattgat gctatgaagt acttttagt gctaatgcct      60
tataaagcat ttatattgca taaatatata atattataat tgacacctag aatctgcaac    120
caggatgtct agagttttaa gaaggaaaat ggtttcgttg cagaggcagc tttgatgaac    180
ccacctccaa gttctgtgtt gcctgtgtga cagaagcatt cgattacctg catcgactag    240
gtattatcta cagagacctg aaaccagaaa acttaattct agatgctgag ggctatctta    300
aattggtaag acaaattctt atcctgtgag atatttctaa acataaagtt gtgctgtagt    360
tgcaattctt ttttttaaa aacttttatt ttaaattaaa aaaatgttta tgtttaattg      420
gtgggtaatt gtttacaatg ttttgttggt ttctgccata caacactgtg aatcagtcat    480
aagtatacat atattccctc cctctagagt cactctctca                           520
```

<210> SEQ ID NO 16
<211> LENGTH: 422
<212> TYPE: DNA
<213> ORGANISM: Bos sp.

<400> SEQUENCE: 16

```
gaaacccctt acgaagttaa acggagattt aaagaagagt gtgagtttta cratctctga     60
agatttcttt gatcttcttt tctaggttga ctttggattt gctaagaaaa taggatctgg    120
acagaaaaca tggacgttct gtggaactcc agagtatgta gctcctgaag tcattctcaa    180
caaaggacat gacttcagtg tggattttg gtccctggga attctagtat atgagctcct    240
cacgggcaag taagtacctt caagttgtgt tcagcctctt cttcagagaa ctgcaaaaat    300
aacttactca tgataataca tacatatata tatatata tatatatata tatatatata    360
tgtatataag aatttaacat tttggaagtg ttttttgatta agcatgatgc cttttcctct    420
tc                                                                    422
```

<210> SEQ ID NO 17
<211> LENGTH: 364
<212> TYPE: DNA
<213> ORGANISM: Bos sp.

<400> SEQUENCE: 17

```
tgggaagccc aaagtagaaa tgattttctt taaatatact ctaactacat agaaaagtac     60
tataagtaaa tacacatata actttaaaat ggcagcagaa ataagaagcc ttcacacttk    120
ccctaaaaac aaaggatttt taatagtcat tctcacctgc aaagcctccg aatcagatcc    180
tcaggtcrtc ttgttatctt tctgggaaaa tccattttttt caatgccttt gagaatcaga    240
ttgtaggtca tcatttggtc aatcccagaa aaaggagggc tagagaaaag ccawaatagg    300
acattaggac ccacatctga gacacattta cagctgatat ccatcctcc ctctttccct     360
ccta                                                                  364
```

<210> SEQ ID NO 18
<211> LENGTH: 318
<212> TYPE: DNA
<213> ORGANISM: Bos sp.

<400> SEQUENCE: 18

```
aagtttcaag atgaccacat tttaaaaata tttctatatt ttctgggcag agaaatatgt     60
acctgtgttt cttaatgtca ttgattccat tcttcagatt tcccagtctt tctgttggat    120
tttgcctaca aaaagagttt tcaatcagct cataataatt atgcttgagt gaattttaca    180
```

| | |
|---|---|
| ttcaaatttt atgctttttc tttatccatt cattgatttt gtcagtaata tgtatmaacc | 240 |
| aggcacattt gtgtacaggg agacagaaaa catatgccct ctctggagga gccacagtcc | 300 |
| aattacagtc agaaatat | 318 |

<210> SEQ ID NO 19
<211> LENGTH: 457
<212> TYPE: DNA
<213> ORGANISM: Bos sp.

<400> SEQUENCE: 19

| | |
|---|---|
| taacttaaat ttaaaaactt aaaawtttta agatctatta tatacataya cttgagtttg | 60 |
| cacacatgat cacacactta aactctgttt acaaaaacac ctagaaaaaa atcaagagag | 120 |
| taatatcagc taccatacct ctctttgtaa aggtgatgga agatttcgtg ctttcagtcc | 180 |
| ctcccaatta aaaccattta accacctgag aaatgagaaa agcacagagg aatattactg | 240 |
| atctgataca ctattagcat gtcatgttat ctgtcaaccc attctgttgc ctgcttcctg | 300 |
| cctscaatgg tgtagctgta agtaatcaga ragaaatact cactgtgccc acamacacac | 360 |
| acacacacac acacgtgtgt atctcacatt aaatccatgc ccactacttt cccgggaggg | 420 |
| ggctttagtg tctccagcag tcagtctagg tctccct | 457 |

<210> SEQ ID NO 20
<211> LENGTH: 1264
<212> TYPE: DNA
<213> ORGANISM: Bos sp.

<400> SEQUENCE: 20

| | |
|---|---|
| acagatcaca gctactttga caagtatcct cctgaaaggg gggtgcctcc agatgagctg | 60 |
| tcaggctggg acaaagactt ctgagagaag ggaagacgat cactgcctac agaatcaaga | 120 |
| ggactagamg tcctagtaat ccaacactga tcatttctmt ttggagtttg acactatctt | 180 |
| ttggaagacc attagagaaa cgaatccctg cccatgatct ggcggggwgg gggggtggkc | 240 |
| gagagtgggt gcagaggtgg ttttgaatta taacgtctca tttagatgct gtgaattatt | 300 |
| catgtgttcc attctttgct tttctcaaat gttgaaggct gtcttagtcc cctcttcaaa | 360 |
| gtcagaacca tttttgktaa agggacatta tcttctctgc aatctattgc tccgtcctta | 420 |
| tcattcttgt cttgtttaag tcctagtaag gtataaaaaa tgtcttgtcc ttgagcaact | 480 |
| aagtcattca aatagaagga agaacaaggg ttaattttgg aaawttttccc tttcccaaca | 540 |
| atctcacgta agcatcaygg catcttgaaa ttgcggtttg caggaaactt gttagtcaat | 600 |
| agaaattctt gatttttacc tgcattcaac ctagaaataa attaatatgc ttctgaaagt | 660 |
| agcctgggga aaggcaaatt tgaatattag tccttggtac cacttcctaa cataaatgag | 720 |
| ttaattcttc cttccaggga attatattrt attggagaac ttagaaaaaa taaacaaagc | 780 |
| aaaaaatatt ttttatttc ccrtgaccag ctgtgggacc tcagagactt tgcaraagtc | 840 |
| ttgtgagagg tggttgtaac gtgtggttaa ttgaggggcc tttggaaaag ttttatctta | 900 |
| catattaaat attttcacra tcaacttaga aaatatgcag aaactagatt gtgaaggctt | 960 |
| ttacttcccc ttacctgtgg aggagaaaaa cttccaaaag gtcaaaatgt tgactctttg | 1020 |
| agactctgag atattttggc cagttctgtg actgttgcta ttaataaacc aagagtatag | 1080 |
| aataaacaca gttaattttt aatgaaaatc ccattggcaa atattgatgc aaaccaaaat | 1140 |
| cactgttgca ttaataattt tttaaaaaga tgtatgagtc atgggactat ttataatttt | 1200 |

-continued

```
agatatgtaa ggcaggccag ccgctcgaga agtaatgccc agtaacaagg acacccgaca    1260
tcaa                                                                  1264

<210> SEQ ID NO 21
<211> LENGTH: 640
<212> TYPE: DNA
<213> ORGANISM: Bos sp.

<400> SEQUENCE: 21
tgctttctga agtgttaaaa cagatgagtg aggccccacc caagaaggtg catccttaac      60
aaattatatt tccacattta gaatcttttt gctgaaccaa agaattttttg tttcctggag    120 tagtattttt aaagttgtac atagatgaag cattttttaat aggatcgacg taacccgctt    180
aatgaatttc taagattttt taaagagttt tatttgcatt tggtttgtaa gcactgtatg    240
tttttccatg tatatatttt tcaattaccc acctataaat gtaggaaatt tatgtattag    300
gttaatatta gaactgtaca gttatactag caatggtatt ctcaaaggtg atcagtagtt    360
gtaattcaaa aacagcttac aaatatacaa ataaaaacca acttagagta ctacaagttt    420
actttggcta tgactggcca tgccattata taatctccac atgtggtttt attgggtttc    480
ctttagagta ctttataaag atgcagaaat gagagaccta accataatat aaacccaatt    540
ctattctgta gctggatgac cttgggaaaa tgacttcact ttttttgagta ctagcttttct    600 cacctgtaga aaaaggcaca ctaaaataat acctacatta                          640

<210> SEQ ID NO 22
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
acaagacgac ct                                                          12

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
acaagatgac ct                                                          12

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aggagggaaa gagggaggat                                                  20

<210> SEQ ID NO 25
<211> LENGTH: 21
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 25
gggaagccca aagtagaaat g                                              21

<210> SEQ ID NO 26
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tttttttttt tttttttttt tttttttttt tttttttttt tttttttttt ttcccagaaa   60
gataacaaga                                                          70
```

GENETIC TEST FOR THE IDENTIFICATION OF DWARFISM IN CATTLE

CROSS-REFERENCE TO RELATED APPLICATION

This application claims priority to U.S. Provisional Patent Application No. 60/733,219 filed Nov. 3, 2005, herein incorporated by reference in its entirety.

FIELD OF THE INVENTION

The present invention relates generally to the genetic condition of dwarfism observed in cattle, particularly Angus. More particularly, the invention relates to molecular markers for identifying potential bovine carriers of the dwarfism mutation and for identifying the genetic locus and mutations thereof responsible for dwarfism and genetic markers test for assaying for the same.

BACKGROUND OF THE INVENTION

Disproportionate dwarfism has been reported in many cattle breeds including Dexter, Holstein, Aberdeen Angus, Hereford and Shorthorn breeds. Dwarfism in American Angus has not been reported since the 1970's until recently when several calves from some sire×dam crosses resulted in phenotypically dwarf calves. Gross and histopathological examination of these calves indicated evidence for diminished endochondral ossification and exhibited other gross features consistent with dwarfism such as the protrusion of the alar wing of the basisphenoid bone into the cranial cavity, abnormalities of the ventral vertebral bodies, and curving of the transverse vertebral processes.

Many researchers have attempted to locate and identify the specific mutations associated with dwarfism, but this has met with only sporadic success. The desire for genetic tests to identify carriers of this condition has long been desirable, but has had limited success. Bovine chondrodysplastic dwarfism in Japanese brown cattle has been the subject of much research, See, for example, Takami, M.; Yoneda, K.; Kobayashi, Y.; Moritomo, Y.; Kata, S. R.; Womack, J. E.; Kunieda, T. "The bovine fibroblast growth factor receptor 3 (FGFR3) gene is not the locus responsible for bovine chondrodysplastic dwarfism in Japanese brown cattle" Animal Genetics: Volume 33(5) October 2002 p 351-355, Until it was ultimately mapped to the distal end of bovine chromosome 6 by linkage analysis. Disease-specific mutations in limbin were identified in affected dwarf calves. This mutation has not been shown to be associated with other types of breeds including Angus, Mishra, B. P.; Reecy, J. M "Mutations in the limbin gene previously associated with dwarfism in Japanese brown cattle are not responsible for dwarfism in the American Angus breed" Animal Genetics: Volume 34(4) August 2003 p 311-312

Presently, the only tool available for dwarfism diagnosis is patho-anatomical diagnosis based on the above described presence of phenotypic characteristics. Thus, there is great demand in the cattle industry for a genetic test that permits the identification of cattle in various breeds that are potential carriers of dwarfism (e.g. before detectable onset of clinical symptoms).

Prior to the present invention, the underlying molecular mechanism of dwarfism in cattle other than Japanese brown cattle has not been isolated or characterized.

It is an object of the present invention to provide a genetic test for dwarfism in Angus and other cattle breeds.

It is yet another object of the present invention to provide the molecular basis for characterizing and further understanding the dwarfism condition in cattle.

It is yet another object of the present invention to use the above information to identify other mutations in linkage disequilibrium with or that are causative of the condition in specific lines, populations or breeds.

Other objects will become apparent from the detailed description of the invention which follows.

SUMMARY OF THE INVENTION

In its broadest aspect, the present invention provides a method for detecting the presence in a bovine subject of a genetic marker associated with dwarfism, comprising the steps of providing a bovine genetic material, and detecting in the genetic material the presence or absence of at least one genetic marker that is in useful linkage disequilibrium with dwarfism trait or a specific nucleotide polymorphism which causes the condition.

According to the invention the inventors have discovered mutation within exon 15 of the cyclic GMP dependant, type-II, protein kinase (PRKG2) gene which is very closely linked to or, most likely is the causal mutation of dwarfism in American Angus cattle. The information was used to create a genetic test for screening for the mutation in cattle or in prospective parental cattle for use in marker assisted breeding.

The invention also provides a novel PRKG2 protein and coding sequence which is truncated and is postulated to be responsible for the dwarf condition in Angus and likely other cattle. The mutant protein allows for the development of in vitro and in vivo models to identify potential agents which will ameliorate the effects of or reverse the condition.

In another aspect of the invention, one may use the PRKG2 gene to screen for other markers in linkage disequilibrium with the SNP of the invention to create further tests, to identify other potential dwarfism disease states in other lines, populations, or breeds.

DETAILED DESCRIPTION OF THE FIGURES

FIG. 1 is an alignment of Human (SEQ ID NO: 2) and Bovine (SEQ ID NO: 1) PRKG2 Exon15 (flanking regions italicized). The analysis was performed at: http://www.ncbi.nlm.nih.gov/blast/b12seq/wblast2.cgi (Tatusova and Madden, 1999); Score=221 bits (115), Expect=9e-55; Identities=131/139 (94%); Strand=Plus/Minus.

FIG. 2 is the full sequence of PRKG2 Exon 15 and flanking introns (italicized)with SNP's indicated in bold) (Sequence shown in reverse complement) (SEQ ID NO: 3). ***Note: The two intronic SNPs are present only in Bos indicus (Brahman) and the exonic SNP (G/A) has only been found in Angus dwarfism carriers to date.

FIG. 3 is the full sequence of bovine PFKG2 showing all SNPs (SEQ ID NOS: 4-21 are disclosed respectively in order of appearance).

FIG. 4 is a diagram showing the samples from 26 American Angus sires, dams and offspring provided by a variety of sources including: breeders, veterinarians, and Universities used in the example.

Figure 5:
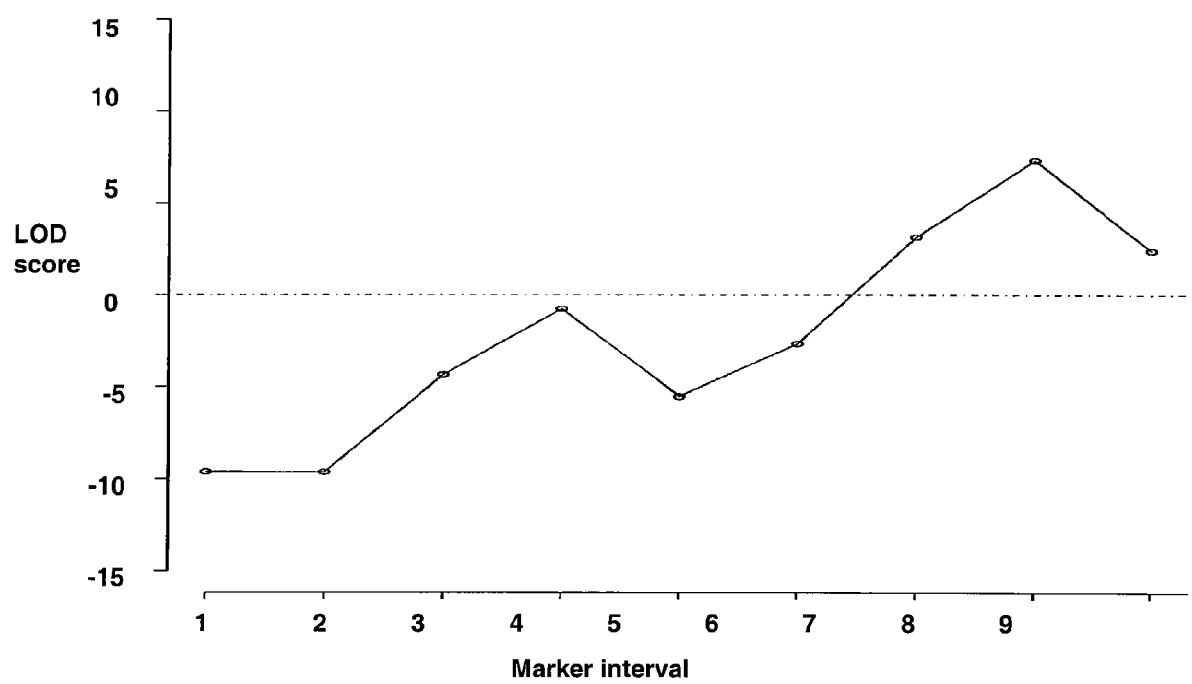

FIG. 5 is genetic map showing the linkage of achondroplasia in American Angus to BTA6. Marker interval 8 shows the strongest association to dwarfism with a LOD=6.89. This marker interval is flanked by markers AFR227 and BM4311 (not shown). The dotted line indicates the significance threshold, LOD=0.

Figure 6:
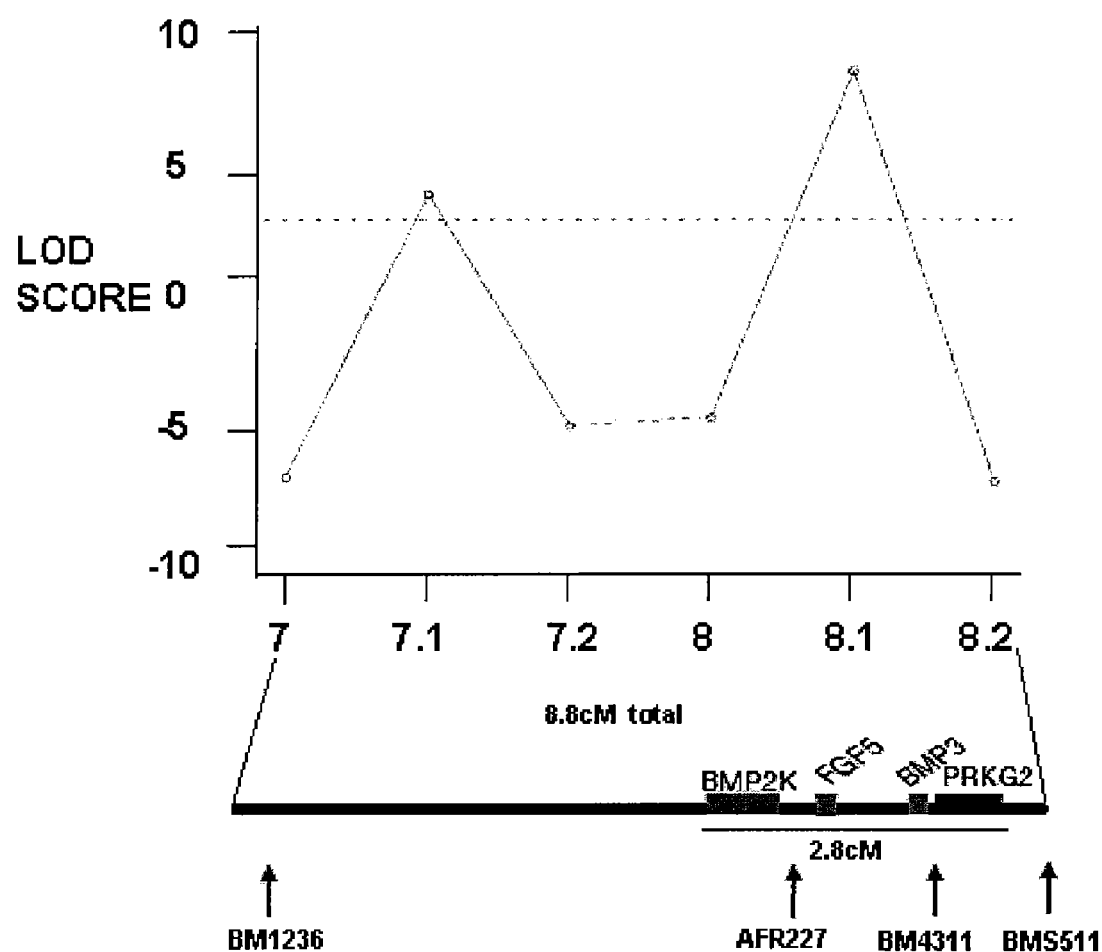

FIG. 6 is a graph showing the linkage analysis of BTA6 upon addition of markers. The graphs suggests a critical region of 2.8 cM between marker interval 8 and 8.2 (AFR227 and BMS511). Association of dwarfism with marker interval 8.1 is significant at LOD=7.88. Marker pair associations are shown only for the critical region and immediately flanking markers. The dotted line indicates the significance threshold, LOD=3.

Figure 7:
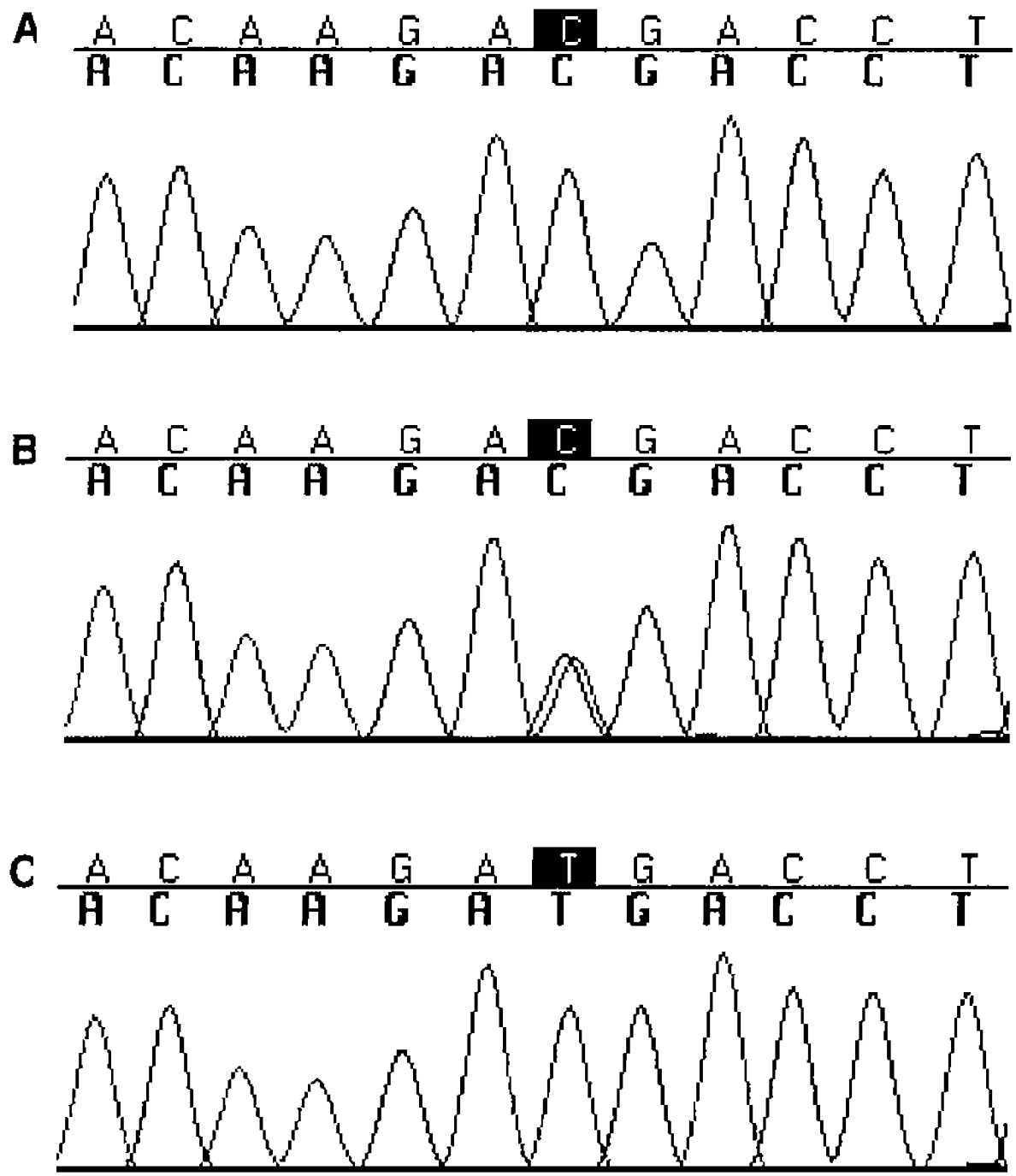

FIG. 7 is a graph showing the sequence of bovine PFKG2. A transition from C→T occurs in exon 15 of PRKG2. (A) A homozygous wild-type (C/C) unaffected individual (SEQ ID NO: 22). (B) A dwarf carrier, heterozygous, possessing the C/T genotype (SEQ ID NO: 22). (C) A dwarf, homozygous (T/T) for the mutant PRKG2 allele (SEQ ID NO: 23).

Figure 8:
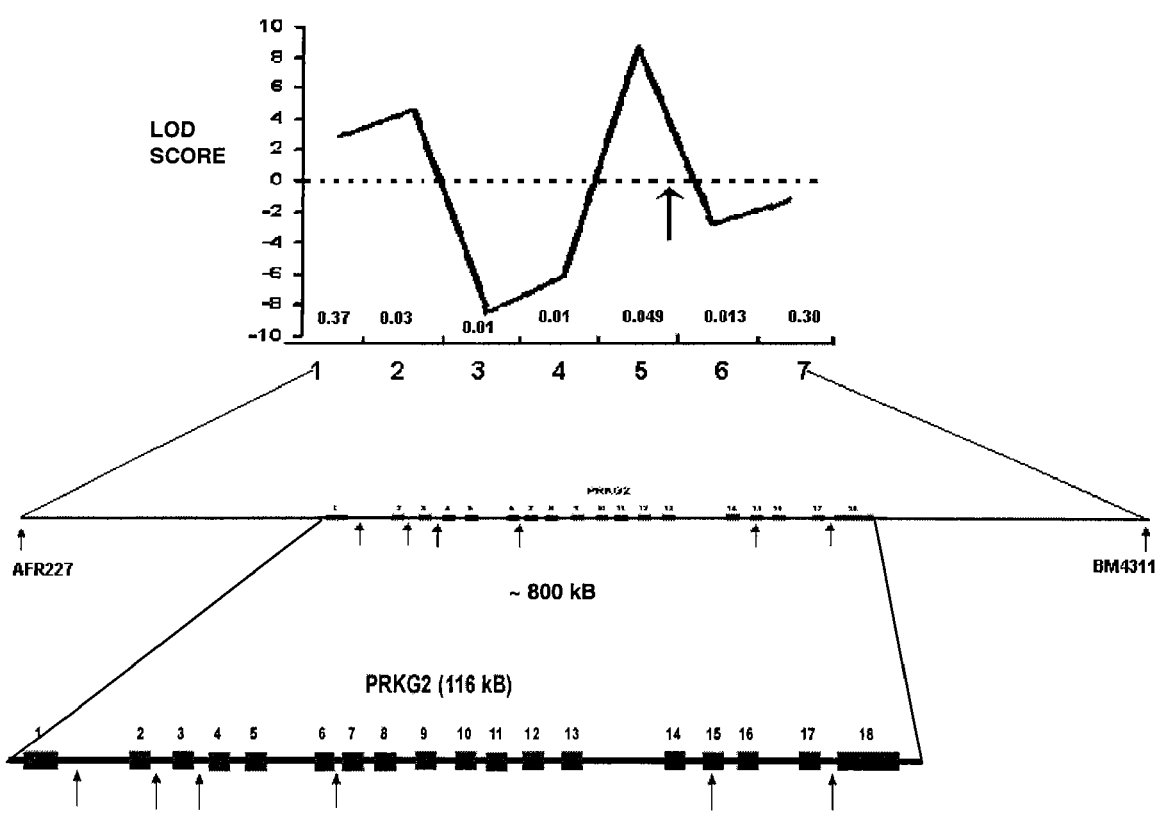

FIG. 8 is a depiction of the linkage analysis of 6 SNPs within PRKG2. (A) The numbers 1-7 represent intervals flanked by marker pairs. The blue arrow indicates the position of the PRKG2 exon 15 mutation. The analysis would suggest the dwarf mutation is at or within the 0.049 cM marker interval 5 (LOD=8.647). Distances between marker intervals are given under the graph in centiMorgans (cM). Below the linkage results is a schematic of marker positions. Red arrows represent SNPs and black arrows represent microsatellites. (B) An enlarged view of the SNP positions within PRKG2. Note, only one mutation, within exon 15, would appear to be present within the coding sequence.

Figure 9:
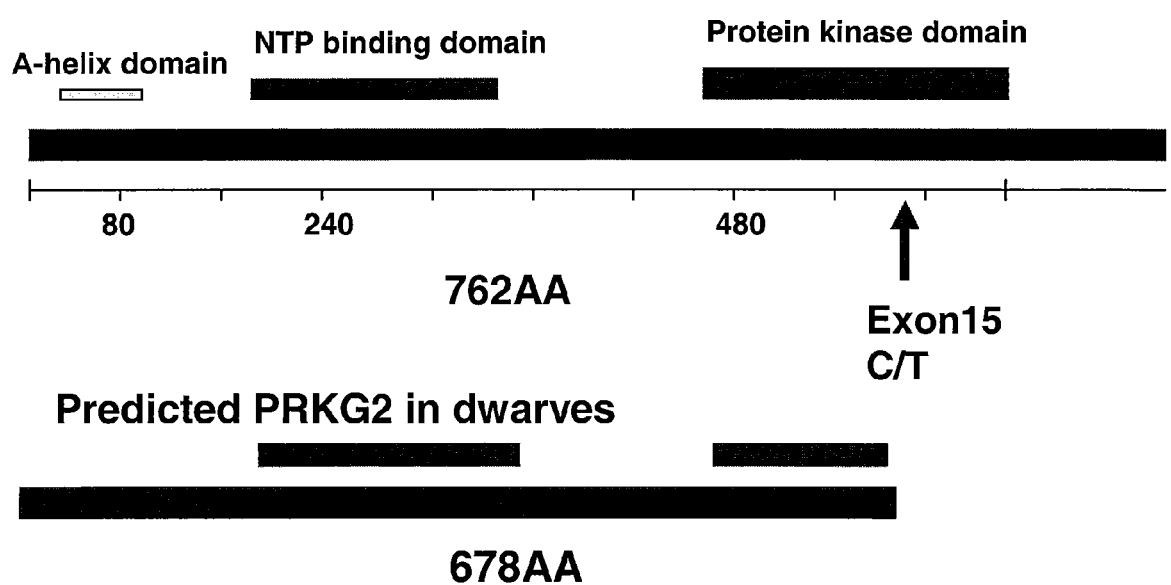

FIG. 9 is a depiction of the protein domains of PRKG2. There are two important structural domains: 1) the cyclic nucleotide binding (NTP_binding) domain which regulates kinase activity upon cGMP binding; and 2) the protein kinase. The full length peptide is 762 amino acids (~87 kDa) and forms a functional homodimer. The position of the exon 15 mutation is indicated by the arrow at AA 678.

DETAILED DISCLOSURE OF THE INVENTION

One primary objective of the present invention is to enable the identification of cattle carrying the dwarfism mutation. This is achieved by a method which detects the presence of a genetic marker in useful linkage disequilibrium with dwarfism in a bovine subject. More specifically, the genetic marker may be the bovine PRKG2 gene.

As used herein, the term a "bovine subject" refers to cattle of any breed. Thus, any of the various cow or ox species, whether male or female, are included in the term, and both adult and new-born animals are intended to be covered. The term does not denote a particular age. One example of a bovine subject is a member of the Holstein-Friesian cattle population.

The term "genetic marker" refers to a variable nucleotide sequence (polymorphic) that is present in bovine genomic DNA on a chromosome and which is identifiable with specific oligonucleotides. Such a variable nucleotide sequence is e.g. distinguishable by nucleic acid amplification and observation of a difference in size or sequence of nucleotides due to the polymorphism. In useful embodiments, such genetic markers may be identified by several techniques known to those skilled in the art, and include typing of microsatellites or short tandem repeats (STR), restriction fragment length polymorphisms (RFLP), detection of deletion or insertion sites, and random amplified polymorphic DNA (RAPD) as well as the typing of single nucleotide polymorphism (SNP) by methods including restriction-fragment-length polymerase chain reaction, allele-specific oligomer hybridization, oligomer-specific ligation assays, mini-sequencing, direct sequencing, fluorescence-detected 5'-exonuclease assays, and hybridization with PNA and LNA probes and others. However, it will be appreciated that other genetic markers and techniques may be applied in accordance with the invention.

As described above, "dwarfism" is a disorder characterized by diminished endochondral ossification and/or other gross features consistent with dwarfism such as the protrusion of the alar wing of the basisphenoid bone into the cranial cavity, abnormalities of the ventral vertebral bodies, and curving of the transverse vertebral processes The method according to the invention includes the provision of a bovine genetic material. Such material include bovine DNA material which may be provided by any conventional method or means. The bovine DNA material may e.g. be extracted, isolated and purified from blood (e.g., fresh or frozen), tissue samples (e.g., spleen, buccal smears), hair samples containing follicular cells and semen.

As previously described, the method of the present invention further comprises a step of detecting in the genetic material the presence or absence of a genetic marker that is linked to a bovine dwarfism trait or preferably is the causative mutation.

In order to detect if the genetic marker is present in the genetic material, standard methods well known to persons skilled in the art may be applied, e.g. by the use of nucleic acid amplification. In order to determine if the genetic marker is genetically linked to the dwarfism trait, a lod score can be applied. A lod score, which is also sometimes referred to as $Z_{max}$, indicates the probability (the logarithm of the ratio of the likelihood) that a genetic marker locus and a specific gene locus are linked at a particular distance. Lod scores may e.g. be calculated by applying a computer program such as the MLINK program of the LINKAGE package (Lathrop et al., 1985). A lod score of greater than 3.0 is considered to be significant evidence for linkage between the genetic marker and the dwarfism trait or gene locus.

In one embodiment of the invention, the genetic marker is located on bovine chromosome bovine chromosome BTA6, between the microsatellites BMS4311 and AFR227 (located at 96.989 cM and 97.728 cM respectively). The region of bovine chromosome BTA6 comprising the genetic markers that are useful in the method of the present invention is indicated In FIG. 5.

Accordingly, genetic markers located on bovine chromosome 6 in the region flanked by and including the polymorphic microsatellite markers BMS4311 and AFR227 (located at 96.989 cM and 97.728 cM respectively), may be useful according to the present invention. In one specific embodiment, the at least one genetic marker is located in the region from about (located at 96.989 cM and 97.728 cM respectively) on bovine chromosome BTA6.

In a further useful embodiment, at least one genetic marker is located on the bovine chromosome BTA6 in the region flanked by and including the polymorphic microsatellite markers BMS4311 and AFR227(located at 96.989 cM and 97.728 cM respectively).

As described in the examples, at least one genetic marker may be linked to a gene causing the bovine dwarfism condition. Thus, in one embodiment, at least one genetic marker is located on bovine chromosome BTA6 in the region flanked by and including the polymorphic microsatellite markers BMS4311 and AFR227 and genetically linked to the dwarfism disease trait, the PRKG2 gene locus. The specific definition and locus of the above polymorphic microsatellite markers can be found in the USDA genetic map (Kappes et al., 1997).

It will be appreciated that in order to detect the presence or absence in a bovine subject of a genetic marker associated with dwarfism, more than one genetic marker may be applied in accordance with the invention. Thus, at least one marker can be a combination of two or more genetic markers which are shown to be informative whereby the accuracy of the test can be increased.

Genetic markers of the present invention can be made using different methodologies known to those skilled in the art. Thus, it will be understood that with the knowledge presented herein, the nucleotide sequences of the above described polymorphic microsatellite markers of bovine chromosome BTA6 have been identified as being genetically linked to the dwarfism gene locus (PRKG2), and additional markers may be generated from the known sequences or the indicated location on bovine chromosome BTA6 for use in the method of the present invention.

For example, using the map illustrated in Appendix B, the dwarfism region of bovine chromosome BTA6 may be microdissected, and fragments cloned into vectors to isolate DNA segments which can be tested for linkage with the dwarfism gene locus. Alternatively, isolated DNA segments can be obtained from the dwarfism region by nucleic add amplification (e.g., polymerase chain reaction) or by nucleotide sequencing of the relevant region of bovine chromosome BTA6 ("chromosome walking").

Genotyping is based on the analysis of genomic DNA which can be provided by using standard DNA extraction methods as described herein. When the genomic DNA is isolated and purified, nucleic add amplification (e.g. polymerase chain reaction) can be used to amplify the region of the DNA corresponding to each genetic marker to be used in the analysis for detecting the presence in a bovine subject of a genetic marker associated with dwarfism.

In another embodiment, the invention comprises a method for identifying genetic markers for the dwarfism condition. Once a major effect gene has been identified, it is expected that other variation present in the same gene, allele or in sequences in useful linkage disequilibrium therewith may be used to identify similar effects on these traits without undue experimentation. The identification of other such genetic variation, once a major effect gene has been discovered, represents more than routine screening and optimization of parameters well known to those of skill in the art and is intended to be within the scope of this invention. This can include other lines, breeds, or even animals which experience dwarfism.

The following is a general overview of techniques which can be used to assay for the polymorphisms of the invention.

In the present invention, a sample of genetic material is obtained from an animal. Samples can be obtained from blood, tissue, semen, etc. Generally, peripheral blood cells are used as the source, and the genetic material is DNA. A sufficient amount of cells are obtained to provide a sufficient amount of DNA for analysis. This amount will be known or readily determinable by those skilled in the art. The DNA is isolated from the blood cells by techniques known to those skilled in the art.

Isolation and Amplification of Nucleic Acid

Samples of genomic DNA are isolated from any convenient source including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue as from a fresh or preserved organ or from a tissue sample or biopsy. The sample can contain compounds which are not naturally intermixed with the biological material such as preservatives, anticoagulants, buffers, fixatives, nutrients, antibiotics, or the like.

Methods for isolation of genomic DNA from these various sources are described in, for example, Kirby, *DNA Fingerprinting, An Introduction*, W. H. Freeman & Co. New York (1992). Genomic DNA can also be isolated from cultured primary or secondary cell cultures or from transformed cell lines derived from any of the aforementioned tissue samples.

Samples of animal RNA can also be used. RNA can be isolated from tissues expressing the major effect gene of the invention as described in Sambrook et al., supra. RNA can be total cellular RNA, mRNA, poly A+ RNA, or any combination thereof. For best results, the RNA is purified, but can also be unpurified cytoplasmic RNA. RNA can be reverse transcribed to form DNA which is then used as the amplification template, such that the PCR indirectly amplifies a specific population of RNA transcripts. See, e.g., Sambrook, supra, Kawasaki et al., Chapter 8 in *PCR Technology*, (1992) supra, and Berg et al., *Hum. Genet.* 85:655-658 (1990).

PCR Amplification

The most common means for amplification is polymerase chain reaction (PCR), as described in U.S. Pat. Nos. 4,683,195, 4,683,202, 4,965,188 each of which is hereby incorporated by reference. If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at 4° C. until use. Cells in other physiological fluids may also be assayed. When using any of these fluids, the cells in the fluid should be separated from the fluid component by centrifugation.

Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, amniocytes from amniotic fluid, cultured chorionic villus cells, or the like are isolated by layering on sterile Ficoll-Hypaque gradient by standard procedures. Interphase cells are collected and washed three times in sterile phosphate buffered saline before DNA extraction. If testing DNA from peripheral blood lymphocytes, an osmotic shock (treatment of the pellet for 10 sec with distilled water) is suggested, followed by two additional washings if residual red blood cells are visible following the initial washes. This will prevent the inhibitory effect of the heme group carried by hemoglobin on the PCR reaction. If PCR testing is not performed immediately after sample collection, aliquots of $10^6$ cells can be pelleted in sterile Eppendorf tubes and the dry pellet frozen at −20° C. until use.

The cells are resuspended ($10^6$ nucleated cells per 100 µl) in a buffer of 50 mM Tris-HCl (pH 8.3), 50 mM KCl 1.5 mM $MgCl_2$, 0.5% Tween 20, 0.5% NP40 supplemented with 100 µg/ml of proteinase K. After incubating at 56° C. for 2 hr. the cells are heated to 95° C. for 10 min to inactivate the proteinase K and immediately moved to wet ice (snap-cool). If gross aggregates are present, another cycle of digestion in the same buffer should be undertaken. Ten µl of this extract is used for amplification.

When extracting DNA from tissues, e.g., chorionic villus cells or confluent cultured cells, the amount of the above mentioned buffer with proteinase K may vary according to the size of the tissue sample. The extract is incubated for 4-10 hrs at 50°-60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in *PCR Technology*, Ehrlich, H. A. (ed.), Stockton Press, New York, which is incorporated herein by reference. PCR can be employed to amplify target regions in very small numbers of cells (1000-5000) derived from individual colonies from bone marrow and peripheral blood cultures. The cells in the sample are suspended in 20 μl of PCR lysis buffer (10 mM Tris-HCl (pH 8.3), 50 mM KCl, 2.5 mM $MgCl_2$, 0.1 mg/ml gelatin, 0.45% NP40, 0.45% Tween 20) and frozen until use. When PCR is to be performed, 0.6 μl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., *Nucleic Acids Res.* 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM $Na_2$ EDTA, pH 8.2). Fifty μl of a 20 mg/ml solution of proteinase K and 150 μl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 μl of the 20 mg/ml proteinase K solution is mixed in the solution and incubated for another night at 37° C. on a gently rocking or rotating platform. Following adequate digestion, one ml of a 6 M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air-dried. The precipitate is placed in distilled water and dissolved.

Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N. H.), DNA Extraction Kit (Stratagene, LaJolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative Biology*, 43:63-67; and Radding, 1982, *Ann. Rev. Genetics* 16:405-436, each of which is incorporated herein by reference).

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, *E. coli* DNA polymerase I or its Klenow fragment, T4 DNA polymerase, Tth polymerase, and Taq polymerase, a heat-stable DNA polymerase isolated from *Thermus aquaticus* and commercially available from Perkin Elmer Cetus, Inc. The latter enzyme is widely used in the amplification and sequencing of nucleic acids. The reaction conditions for using Taq polymerase are known in the art and are described in Gelfand, 1989, *PCR Technology*, supra.

Allele Specific PCR

Allele-specific PCR differentiates between target regions differing in the presence of absence of a variation or polymorphism. PCR amplification primers are chosen which bind only to certain alleles of the target sequence. This method is described by Gibbs, *Nucleic Acid Res.* 17:12427-2448 (1989).

Allele Specific Oligonucleotide Screening Methods

Further diagnostic screening methods employ the allele-specific oligonucleotide (ASO) screening methods, as described by Saiki et al., *Nature* 324:163-166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed that under low stringency will bind to both polymorphic forms of the allele, but which at high stringency, bind to the allele to which they correspond. Alternatively, stringency conditions can be devised in which an essentially binary response is obtained, i.e., an ASO corresponding to a variant form of the target gene will hybridize to that allele, and not to the wild type allele.

Ligase Mediated Allele Detection Method

Target regions of a test subject's DNA can be compared with target regions in unaffected and affected family members by ligase-mediated allele detection. See Landegren et al., *Science* 241:107-1080 (1988). Ligase may also be used to detect point mutations in the ligation amplification reaction described in Wu et al., *Genomics* 4:560-569 (1989). The ligation amplification reaction (LAR) utilizes amplification of specific DNA sequence using sequential rounds of template dependent ligation as described in Wu, supra, and Barany, *Proc. Nat. Acad. Sci.* 88:189-193 (1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature (TM). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., *PCR Technology, Principles and Applications for DNA Amplification*, W. H. Freeman and Co., New York (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., *Meth. Enzymol.* 155:501-527 (1986), and Myers et al., in *Genomic Analysis, A Practical Approach*, K. Davies Ed. IRL Press Limited, Oxford, pp. 95-139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis

Target sequences or alleles at an particular locus can be differentiated using single-strand conformation polymorphism analysis, which identifies base differences by alteration in electrophoretic migration of single stranded PCR products, as described in Orita et al., *Proc. Nat. Acad. Sci.* 85:2766-2770 (1989). Amplified PCR products can be generated as described above, and heated or otherwise denatured, to form single stranded amplification products. Single-stranded nucleic acids may refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, as described in Grompe et al., *Am. J. Hum. Genet.* 48:212-222 (1991). In another method, differences between target sequences can be detected by enzymatic cleavage of mismatched base pairs, as described in Nelson et al., *Nature Genetics* 4:11-18 (1993). Briefly, genetic material from an animal and an affected family member may be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms that may be associated with polymorphisms.

Non-Gel Systems

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e. there is a mismatch of some form; the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Yet another technique includes an Invader Assay which includes isothermic amplification that relies on a catalytic release of fluorescence. See Third Wave Technology at www.twt.com.

Non-PCR Based DNA Diagnostics

The identification of a DNA sequence linked to an allele sequence can be made without an amplification step, based on polymorphisms including restriction fragment length polymorphisms in an animal and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with 32P or 35S. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to a bovine chromosome where one of the major effect genes resides, and thus defining a genetic marker linked to one of the major effect genes, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Preferred tandem repeat hybridization probes for use according to the present invention are those that recognize a small number of fragments at a specific locus at high stringency hybridization conditions, or that recognize a larger number of fragments at that locus when the stringency conditions are lowered.

One or more additional restriction enzymes and/or probes and/or primers can be used. Additional enzymes, constructed probes, and primers can be determined by routine experimentation by those of ordinary skill in the art and are intended to be within the scope of the invention.

Although the methods described herein may be in terms of the use of a single restriction enzyme and a single set of primers, the methods are not so limited. One or more additional restriction enzymes and/or probes and/or primers can be used, if desired. Indeed in some situations it may be preferable to use combinations of markers giving specific haplotypes. Additional enzymes, constructed probes and primers can be determined through routine experimentation, combined with the teachings provided and incorporated herein.

According to one embodiment of the invention, polymorphisms in a major effect gene has been identified which have an association with dwarfism. The presence or absence of the markers, in one embodiment may be assayed by PCR RFLP analysis using if needed, restriction endonucleases, and amplification primers which may be designed using analogous human, pig or other of the sequences due to the high homology in the region surrounding the polymorphisms, or may be designed using known sequences (for example, human) as exemplified in GenBank or even designed from sequences obtained from linkage data from closely surrounding genes based upon the teachings and references herein. The sequences surrounding the polymorphism will facilitate the development of alternate PCR tests in which a primer of about 4-30 contiguous bases taken from the sequence immediately adjacent to the polymorphism is used in connection with a polymerase chain reaction to greatly amplify the region before treatment with the desired restriction enzyme. The primers need not be the exact complement; substantially equivalent sequences are acceptable. The design of primers for amplification by PCR is known to those of skill in the art and is discussed in detail in Ausubel (ed.), *Short Protocols in Molecular Biology*, Fourth Edition, John Wiley and Sons 1999. The following is a brief description of primer design.

Primer Design Strategy

Increased use of polymerase chain reaction (PCR) methods has stimulated the development of many programs to aid in the design or selection of oligonucleotides used as primers for PCR. Four examples of such programs that are freely available via the Internet are: PRIMER by Mark Daly and Steve Lincoln of the Whitehead Institute (UNIX, VMS, DOS, and Macintosh), Oligonucleotide Selection Program (OSP) by Phil Green and LaDeana Hiller of Washington University in St. Louis (UNIX, VMS, DOS, and Macintosh), PGEN by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Sequencing and PCR Primers

Designing oligonucleotides for use as either sequencing or PCR primers requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding program such as those described above (see prediction of Nucleic Acid Structure). If a possible stem structure is observed, the sequence of the primer can be shifted a few nucleotides in either direction to minimize the predicted secondary structure. The sequence of the oligonucleotide should also be compared with the sequences of both strands of the appropriate vector and insert DNA. Obviously, a sequencing primer should only have a single match to the target DNA. It is also advisable to exclude primers that have only a single mismatch with an undesired target DNA sequence. For PCR primers used to amplify genomic DNA, the primer sequence should be compared to the sequences in the GenBank database to determine if any significant matches occur. If the oligonucleotide sequence is present in any known DNA sequence or, more importantly, in any known repetitive elements, the primer sequence should be changed.

The methods and materials of the invention may also be used more generally to evaluate animal DNA, genetically type individual animals, and detect genetic differences in animals. In particular, a sample of animal genomic DNA may be evaluated by reference to one or more controls to determine if a polymorphism in one of the sequences is present. Preferably, RFLP analysis is performed with respect to the animal's sequences, and the results are compared with a control. The control is the result of a RFLP analysis of one or both of the sequences of a different animal where the polymorphism of the animal gene is known. Similarly, the genotype of an animal may be determined by obtaining a sample of its genomic DNA, conducting RFLP analysis of the gene in the DNA, and comparing the results with a control. Again, the control is the result of RFLP analysis of one of the sequences of a different animal. The results genetically type the animal by specifying the polymorphism(s) in its gene. Finally, genetic differences among animals can be detected by obtaining samples of the genomic DNA from at least two animals, identifying the presence or absence of a polymorphism in one of the nucleotide sequences, and comparing the results.

These assays are useful for identifying the genetic markers relating to growth and meat quality, as discussed above, for identifying other polymorphisms in the same genes or alleles that may be correlated with other characteristics, and for the general scientific analysis of animal genotypes and phenotypes.

One of skill in the art, once a polymorphism has been identified and a correlation to a particular trait established will understand that there are many ways to genotype animals for this polymorphism. The design of such alternative tests merely represents optimization of parameters known to those of skill in the art and is intended to be within the scope of this invention as fully described herein.

In accordance with the present invention there may be employed conventional molecular biology, microbiology, and recombinant DNA techniques within the skill of the art. Such techniques are explained fully in the literature. See, e.g., Maniatis, Fritsch & Sambrook, *Molecular Cloning: A Laboratory Manual* (1982); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription and Translation* (B. D. Hames & S. J. Higgins eds. (1984)); *Animal Cell Culture* (R. I. Freshney, ed. (1986)); *Immobilized Cells And Enzymes* (IRL Press, (1986)); B. Perbal, *A Practical Guide To Molecular Cloning*, (1984).

The invention also includes novel nucleotide and protein sequences which are associated with dwarfism. This molecular information can be used in a variety of methods for studying the effects of, the causes of, and possibly the reversal or treatment of this condition in vitro and in vivo.

In another embodiment, the invention comprises a method for identifying a genetic marker for dwarfism in a particular line, strain, breed, population or animal. Based upon the highly conserved nature of this gene among different animals and the location of the polymorphisms within these highly conserved regions, is it expected that with no more than routine testing as described herein this marker can be applied to different animal species to select for dwarfism based on the teachings herein. For other animals in which sequences are available a BLAST comparison of sequences may be used to ascertain whether the particular allele is analogous to the one disclosed herein. The analogous polymorphism will be present in other animals and in other closely related genes. The term "analogous polymorphism" shall be a polymorphism which is the same as any of those disclosed herein as determined by BLAST comparisons using the default parameters.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, CABIOS 5:151-153 (1989); Corpet, et al., *Nucleic Acids Research* 16:10881-90 (1988); Huang, et al., *Computer Applications in the Biosciences* 8:155-65 (1992), and Pearson, et al., *Methods in Molecular Biology* 24:307-331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information world wide web at hcbi.nlm.nih.gov/).

It is also possible to establish linkage between specific alleles of alternative DNA markers and alleles of DNA markers known to be associated with a particular gene (e.g. the PRKG2 gene discussed herein), which have previously been shown to be associated with a particular trait. Thus, in the present situation, taking the PRKG2 gene, it would be possible, at least in the short term, to select for animals likely to not exhibit dwarfism, indirectly, by selecting for certain alleles of a PRKG2 associated marker through the selection of specific alleles of alternative chromosome markers. As used herein the term "genetic marker" shall include not only the polymorphism disclosed by any means of assaying for the protein changes associated with the polymorphism, be also linked markers, use of microsatellites, or even other means of assaying for the causative protein changes indicated by the marker and the use of the same to influence the dwarfism tendencies of an animal.

EXAMPLE 1

Bovine PRKG2 Sequence

Sequence of bovine genes was generated by sequencing of genomic DNA. Template sequence for PCR primer design was obtained through mining of the preliminary bovine genomic draft sequence by BLAST analysis. Primers were designed using Primer3 at http://frodo.wi.mit.edu/cgi-bin/primer3/primer3 www.cgi (Rozen and Skaletsky, 2000). The sequences of all human genes within a 5 Mb critical region defined by the human/bovine radiation hybrid panel (Everts-van der Wind et al., 2005) were used as template sequence for BLAST analysis. Human sequence was obtained from the UCSC genome server at http://www.genome.ucsc.edu/ (Karolchik et al., 2003; Kent et al., 2002) and sequences were cross referenced with a second gene prediction source from ensemble at http://www.ensembl.org/index.html. We applied CAP3 to assemble flanking sequences of genes into small contigs for primer design when needed (Huang and Madan, 1999). Four genes were identified as positional candidates, including: BMP2K, BMP3, FGF5, PRKG2. More than 80 SNPs were discovered within and surrounding these genes; however, only a single mutation was discovered within an exon. This C/T missense mutation within the exon 15 kinase domain of PRKG2 was PCR amplified and initially genotyped by DNA sequencing (FIG. 1).

FIG. 1 shows the alignment of Human and Bovine PRKG2 Exon15 flanking intron regions are in italics. The analysis was performed at: http://www.ncbi.nlm.nih.gov/blast/b12seq/wblast2.cgi FIG. 2 is the full sequence of PRKG2 Exon 15 and flanking introns (flaking regions in italics) with SNP's indicated (in bold) (Sequence shown here in reverse complement)

The two intronic SNPs are present only in Bos indicus (Brahman) and the exonic SNP (G/A) has only been found in Angus dwarfism carriers.

Protocol for Genotyping of PRKG2 Exon 15

Thermocycling Conditions:

Samples were denatured for 5 minutes at 95 C, followed by 36 cycles of 95 C for 30 sec, 60 C for 75 sec, and 72 C for 75 sec. To conclude, samples were incubated at 72 C for 10 min. Template was stored at 4 C.

```
Primer sequence:
BTPRKG15cF 5' primer 5' AGGAGGGAAAGAGGGAGGAT 3'
(SEQ ID NO:24)

BTPRKG15cR 3' primer 5' GGGAAGCCCAAAGTAGAAATG 3'
(SEQ ID NO:25)
```

| Reagent conditions: | |
|---|---|
| Reagents | Volume (uL) |
| 10× buffer* (Promega) | 1 |
| MgCl2 25 mM(Promega) | 0.8 |
| dNTPs 10 mM (Invitrogen) | 0.2 |
| 5' Primer 50 nM (IDT) | 0.2 |
| 3' Primer 50 nM(IDT) | 0.2 |
| Taq 10 U/uL (Promega) | 0.1 |

| -continued | |
|---|---|
| Reagent conditions: | |
| Reagents | Volume (uL) |
| DNA (25 ng/uL) | 0.5 |
| Deionized water (Gibco) | 7 |
| TOTAL VOLUME | 10 |

*10×Buffer diluted 1:10 consists of 0.1% Trition X-100, 10 mM Tris-HCL (pH 9.0), and 50 mM KCl.

Subsequently, a protocol was developed using single base extension to determine the genotype at this locus (see below). This method is still in preliminary development. We are in the process of testing efficacy, precision, and accuracy based on genotyping results from known carriers, dwarfs, and non-carriers. We are also seeking to test additional breeds to determine if our method can detect dwarfism in other genetic backgrounds.

Single Base Extension Genotyping Protocol by SNaPshot (Applied Biosystems)

```
Primer Sequence
5'- TTT TTT TTT TTT TTT TTT TTT TTT TTT TTT TTT

TTT TTT TTT TTT TTT TTT TCC CAG AAA GAT AAC AAG

A -3' (SEQ ID NO:26)
```

General procedure
1) PCR was performed as described above.
2) PCR was cleaned up using Exosapit (Amersham). Two units (2 uL) exosapit was added to 5 μL of PCR product. The sample was then incubated at 37° C. for 1 hour, followed by 75° C. for 15 minutes to inactivate the enzymes. Template was then stored on ice or at 4° C.
3) SNaPshot master mix, positive and negative controls were prepared as described below. The dwarf marker can be run by itself or in multiplex with additional SNaPshot markers, reducing genotyping costs if additional markers warrant genotyping. To multiplex, primers need to be tailed on the end opposite of the SNP such that the full primer length is at least 4 base pairs different from all other primers.
4) One positive and one negative SNaPshot control were run with each multiplex kit. The negative control contains all of the SNaPshot multiplex solution, but contains no DNA. The positive control consists of a multiplex control primer mix which contains six distinct primers and control template (an amplicon from CEPH DNA).

Thermal Cycling and Post-Extension Treatment

The following program is used to conduct thermal cycling reaction:
1. 96° C. for 10 seconds
2. 50° C. for 5 seconds
3. 60° C. for 30 seconds
4. Repeat steps 1 through 3 for 24 more cycles.
5. Store product at 4° C.
6. Removal of the 5' phosphoryl groups requires addition of 1.0 unit of Shrimp Alkaline Phosphatase (SAP) followed by incubation at 37° C. for 1 hour. SAP enzyme is then deactivated by incubation at 75° C. for 15 minutes.
7. Products are then analyzed on an ABI-3100 and results loaded into Genescan® software for analysis.

| SNaPshot Master Mix | |
|---|---|
| Reagents | Volume (uL) |
| SNaPshot multiplex ready reaction mix | 5 |
| PCR product(s) (0.01-0.40 pM) | 3 |
| PCR primer(s) (0.2 uM) | 1 |
| Deionized water | 1 |
| TOTAL VOLUME | 10 |

| SNaPshot Control master Mixes | | |
|---|---|---|
| Reagent | Positive control (uL) | Negative control (uL) |
| SNaPshot multiplex ready reaction mix | 5 | 5 |
| SNaPshot multiplex control primer mix | 1 | 1 |
| SNaPshot multiplex control template | 2 | 0 |
| Deionized water | 2 | 4 |
| TOTAL VOLUME | 10 | 10 |

The full gene sequence is provided in FIG. 3.

FIG. 3.

Bovine Sequence of PRKG2

Regions flanking the Exons are in italics, SNPs bolded Alignment between bovine sequences and human is provided in FIG. 1

***NOTE: These sequences are not all in 5'-3' orientation. Some are reverse reads.

To date, we have sequenced all of PRKG2, except the 5' untranslated region and exon 7 which we have been unable to amplify. Additional information regarding the methods used to discover the mutation in PRKG2 is described in the Examples. All SNPs and markers discovered to date in all 4 candidate genes are included in Example 4.

REFERENCES

Everts-van der Wind, A., S. R. Kata, M. R. Band, M. Rebeiz, D. M. Larkin, R. E. Everts, C. A. Green, L. Liu, S. Natarajan, T. Goldammer, J. H. Lee, S. McKay, J. E. Womack, and H. A. Lewin. A 1463 gene cattle-human comparative map with anchor points defined by human genome sequence coordinates. Genome Research 14; 1424-1437.

Huang, X., and A. Madan. 1999. CAP3: A DNA sequence assembly program. Genome Research. 9: 868-877.

Rozen, S. and H. J. Skaletsky. 2000. Primer3 on the WWW for general users and for biologist programmers. In: Krawetz S, Misener S (eds) Bioinformatics Methods and Protocols: Methods in Molecular Biology. Humana Press, Totowa, N. J., pp 365-386.

Karolchik, D., Baertsch, R., Diekhans, M., Furey, T. S., Hinrichs, A., Lu, Y. T., Roskin, K. M., Schwartz, M., Sugnet, C. W., Thomas, D. J., Weber, R. J., Haussler, D. and Kent, W. J. 2003. The UCSC Genome Browser Database. Nucl. Acids Res 31(1), 51-54.

Kent, W. J., Sugnet, C. W., Furey, T. S., Roskin, K. M., Pringle, T. H., Zahler, A. M., and Haussler, D. 2002. The Human Genome Browser at UCSC. Genome Res. 12(6), 996-1006.

Tatiana, T. A., and T. L. Madden. 1999. Blast 2 sequences—a new tool for comparing protein and nucleotide sequences. FEMS Microbiol Lett. 174:247-250.

EXAMPLE 3

Summary of Results

A mutation within exon 15 of the cyclic GMP dependant, type-II, protein kinase (PRKG2) is most likely the causal mutation of dwarfism in American Angus cattle. Three key lines of evidence suggest that this mutation is causal. These include: 1) 100% concordance of the mutation with dwarf and carrier phenotypes within our pedigree; 2) the mutation is predicted to cause a premature stop codon within the functional kinase domain of PRKG2 required for SOX9 regulation of growth plate development; 3) knockout and naturally occurring PRKG2 mutants are dwarfs with similar patterns of inheritance, and disrupted growth plates as American Angus. The evidence supporting the functionality of this mutation warrants additional research to verify causality of the mutation we describe. This would provide a body of evidence that would be sound in a court of law should anyone dispute the validity of this mutation.

Overview of Research/Analysis

Blood/tissue and phenotype: Samples from 26 American Angus sires, dams and offspring were provided by a variety of sources including: breeders, veterinarians, and Universities (see FIG. 4). All samples were sent to Iowa State University where DNA was isolated, quantitated, and quality checked. Animal phenotype (dwarf or normal) was provided by third parties (breeders and veterinarians).

Preliminary genotyping: In order to evaluate the possibility that the gene responsible for dwarfism in American Angus cattle was the same as that in other breeds, we genotyped affected and unaffected individuals for two known mutations. The first gene evaluated was Limbin. Briefly, the known limbin mutation present in Japanese Brown cattle were not present in American Angus dwarfs. Thus, these mutations cannot be responsible for dwarfism in American Angus. The results of this study were published in Animal Genetics (Mishra and Reecy, 2003).

Next, we evaluated mutations know to cause dwarfism in Dexter cattle. For this study, DNA was sent to Australia for genotyping and CRC for Innovative Dairy Products, The University of Sydney, Camden, NSW, Australia. These mutations were not present in our American Angus samples. In addition, we completed a microsatellite analysis of this region to test for loss of heterozygosity. Again, the results were negative. Thus, the gene responsible for dwarfism in Dexter Cattle is different than that in American Angus cattle. Results of this genotyping are not included in this report, because the mutations and microsatellites tested were coded such that we cannot say what or where they are. This was done to maintain confidentiality, because there is a patent currently in review for these mutations.

Whole genome scan: At the completion of the preliminary studies, it was decided that a whole genome scan was the best way to proceed in the identification of markers associated with American Angus dwarfism. Toward this end, DNA was sent to University of Leige, Belgium for microsatellite genotyping. Intermittently there after, genotype information was forwarded to us. We compiled and coded this information for statistical analysis (see FIG. 6: data for BTA1, 6, 14 and 19).

Statistical Analysis: A program was written based on the methods of Elston and Stewart and Fernandez et al. (Elston and Stewart, 1971; Fernandez et al., 2001). With the use of this program the limitation of the small pedigree was overcome. This methodology relies upon the Elston-Stewart algorithm. For each marker interval, a likelihood of odds (LOD) score was calculated to determine the statistical association between the given marker interval and the dwarfism phenotype. The LOD score was calculated as the log base 10 of the likelihood ratio of (L1/L2) assuming: 1) the dwarf gene is at the center of the flanking markers (L1), and 2) the dwarf gene is on another chromosome (L2). If we reject the null hypothesis that the dwarf gene is on another chromosome when the LOD score is greater than 3, then the probability of a false positive is lower than 0.05.

The results of this statistical analysis indicated that the dwarfism mutation is on bovine chromosome 6, between the microsatellites BMS4311 and AFR227 (See Appendix B). Furthermore, when looking at individual genotypes at these microsatellite markers, there is a complete loss of heterozygosity at BMS4311 (all six dwarfs are homozygotic) and almost complete loss at AFR227 (5 of 6 dwarfs were homogygous). When looking at all non-affected animals this was never the case. This evidence further supported that this marker interval is the region of interest.

Fine-mapping: Additional markers were genotyped between, and closely flanking those used in the initial analysis. Analysis of the new markers indicated linkage confined within a 2.8 centiMorgan (cM) region flanked by the markers AFR227, and BMS511 (see FIG. 6). The maximum LOD score within this chromosomal segment was 7.88, and was localized again within the region flanked by markers AFR227 and BM4311. No additional microsatellite markers were known to occur in this region, leading us to pursue positional candidate genes.

Analysis of positional candidate genes: Human-bovine radiation hybrid mapping data suggested 20 known genes, and 16 pseudeogenes within the critical region. Four genes, bone morphogenetic protein 2 kinase (BMP2K) (Kearns et al., 2001 Genbank Accession number NM 080708), bone morphogenetic protein 3 (BMP3) (Bahamonde and Lyons, 2001 Genbank Accession number 173404), fibroblast growth factor 5 (FGF5) (Colvin et al., 1996; Liu et al., 2002), and PRKG2 (Pfeifer et al., 1996 Genbank Accession number NM 008926) were selected as candidates based on specific, or indirect evidence of their effects on bone.

Upon sequencing, only one single nucleotide polymorphism (SNP), a Cytosine (C) to Thiamine (T) transition within PRKG, was discovered within an exon (see FIG. 7). No coding mutations or mutations that are in concordance with the recessive pattern of inheritance of dwarfism have been discovered in the other genes at this time.

Evidence supporting PRKG2 as the putative causal mutation: The PRKG2 mutation shows 100% concordance with phenotype, and dwarf carrier status within our mapping population. FIG. 8 shows a linkage analysis of 6 SNPs in PRKG2, including the exon 15 mutation. The LOD score is maximized at 8.647 for the marker interval between an SNP in the $6^{th}$ intron and the $15^{th\ exon}$. The C/T transition mutation is predicted to cause a nonsense mutation that truncates PRKG2 85 amino acids prematurely. The mutation removes the 25 C-terminal amino acids from PRKG2's kinase domain (see FIG. 9).

Cyclic-guanidine monophosphate dependant, type II, protein kinase (PRKG2)

PRKG2 acts as a "molecular switch" for the transition from the proliferative to hypertrophic state in osteocytes in the rat (Chikuda et al., 2004). Mutations in PRKG2 cause disruption of endochondral ossification and achondroplasia in both the mouse and rat (Pfeifer et al., 1996; Chikuda et al., 2002; appended) with a phenotype similar to that observed in cattle. Chikuda et al. (2004) provide strong evidence that PRKG2's kinase function is necessary to block SOX9 nuclear translocation, and inappropriate expression of proliferative growth markers in chondrocytes. The SOX9 pathway is important in chondrocyte development, suggesting that a regulator, such as PRKG2, would drastically alter chondrocyte development and endochondral ossification (Akiyama et al., 2004; Akiyama et al., 2002; Bi et al., 2001; Chikuda et al., 2004).

REFERENCES

Akiyama, H., M. C. Chaboissier, J. F. Martin, A. Schedl, and B. de Crombrugghe. 2002. The transcription factor sox9 has essential roles in successive steps of the chondrocyte differentiation pathway and is required for expression of sox5 and sox6. Genes Dev 16: 2813-2828.

Akiyama, H. et al. 2004. Interactions between sox9 and beta-catenin control chondrocyte differentiation. Genes Dev 18: 1072-1087.

Bi, W. et al. 2001. Haploinsufficiency of sox9 results in defective cartilage primordia and premature skeletal mineralization. Proc Natl Acad Sci USA 98: 6698-6703.

Bahamonde, M. E., and K. M. Lyons. 2001. Bmp3: To be or not to be a bmp. J Bone Joint Surg Am 83-A Suppl 1: S56-62.

Colvin, J. S., B. A. Bohne, G. W. Harding, D. G. McEwen, and D. M. Ornitz. 1996. Skeletal overgrowth and deafness in mice lacking fibroblast growth factor receptor 3. Nat Genet 12: 390-397.

Elston, R. C. and J. Stewart. 1971. A general model for the genetic analysis of pedigree data. *Hum Hered* 21: 523-542.

Fernandez, S. A., R. L. Fernando, B. Guldbrandtsen, L. R. Totir, and A. L. Carriquiry. 2001. Sampling genotypes in large pedigrees with loops. *Genet Sel Evol* 33: 337-367.

Kearns, A. E., M. M. Donohue, B. Sanyal, and M. B. Demay. 2001. Cloning and characterization of a novel protein kinase that impairs osteoblast differentiation in vitro. J Biol Chem 276: 42213-42218.

Liu, Z., J. Xu, J. S. Colvin, and D. M. Ornitz. 2002. Coordination of chondrogenesis and osteogenesis by fibroblast growth factor 18. Genes Dev 16: 859-869.

Mishra, B. P. and J. M. Reecy. 2003. Mutations in the limbin gene previously associated with dwarfism in Japanese brown cattle are not responsible for dwarfism in the American Angus breed. Animal Genetics 34(4):311-2.

EXAMPLE 4

List of All SNPs found as of to date in candidate genes for dwarfism (Position numbers based upon Genbank references NM 173404, NM 080708, or NM 008926 as applicable)

| | | PRKG2 SNPs | | |
|---|---|---|---|---|
| Exon | Position | SNP | Breed | ID# |
| 1 | 719 | C/T | Brahman | BR7 |
| | 746 | A/G | ANGUS | 9C40 |
| 2 | No SNP | | | |
| 3 | 642 | C/T | ANGUS | 9C40 |
| | 674 | C/T | ANGUS | 9C40 |
| 4 | 264 | A/G | ANGUS | 9C40 |
| | 294 | C/T | ANGUS | 9C40 |
| | | C/T | Brahman | BR7 |
| | 311 | A/G | ANGUS | 9C40 |

-continued

PRKG2 SNPs

| Exon | Position | SNP | Breed | ID# |
|---|---|---|---|---|
| 5 | 23 | C/C | ANGUS | |
| | | T/T | Brahman and Herford | |
| | 356 | A/A | ANGUS | |
| | | A/G | BRAHMAN | |
| | | G/G | Herford | |
| | 375 | INS AT | Brahman and Herford | |
| | | DEL/DEL | ANGUS | |
| | 383 | INS C | Brahman and Herford | |
| | | DEL/DEL | ANGUS | |
| | 386 | INS A | Brahman and Herford | |
| | | DEL/DEL | ANGUS | |
| | 391 | A/A | Brahman and Herford | |
| | | C/C | ANGUS | |
| | 398 | A/A | ANGUS | 257 |
| | | A/G | ANGUS, HER, BRAM | 8242 |
| | | G/G | ANGUS | 9C40 |
| | 409 | A/A | ANGUS | 257 |
| | | A/G | ANGUS | 9C40 |
| | | G/G | 8242, HER, BRAHM | |
| 6 | 315 | A/A | ANGUS, HER, BRAHM | 8242 |
| | | A/C | ANGUS | 9C40 |
| | | C/C | ANGUS | 257 |
| | 344 | C/C | ANGUS, HER, BRAHM | 8242 |
| | | C/T | ANGUS | 9C40 |
| | | T/T | ANGUS | 257 |
| | 434 | C/C | ANGUS | 257 |
| | | T/T | ANGUS, HER, BRAHM | 8242 |
| | | C/T | ANGUS | 9C40 |
| | 487 | C/C | ANGUS | 257 |
| | | T/T | ANGUS, HER, BRAHM | 8242 |
| | | C/T | ANGUS | 9C40 |
| 7 | NOT AVAILABLE | | | |
| 8 | No SNP | | | |
| 9 | 464 | T/G | BRAHMAN | |
| 10 | 488 | A/T | BRAHMAN | 9C40 |
| | 630 | T/C | BRAHMAN | 9C40 |
| 11 | 676 | A/A | Angus and Brahman | |
| | | T/T | Herford | HH846 |
| 12 | 503 | G/T | Brahman | BR7 |
| 13 | No SNP | | | |
| 14 | 53 | A/G | BRAHMAN | |
| | | A/A | ANGUS | 257 |
| | 275 | INS G | BRAHMAN | |
| | | INSG/DEL | ANGUS | 9C40, 8242, 257 |
| | | DEL/DEL | Herford | |
| | 319 | INS ACAC | Herford | |
| | | DEL/DEL | Angus and Brahman | |
| | 325 | Msat 12 bps | Herford (hetero) | |
| | | monomorph | Angus and Brahman | |
| 15 | 120 | T/G | BRAHMAN | |
| | | T/T | ANGUS AND HEREFORD | |
| | 188 | A/G | ANGUS | 9C40 |
| | | A/A | ANGUS | 257 |
| | | G/G | ANGUS, HER, BRAM | 8242 |
| | 294 | A/T | BRAHMAN | |
| | | T/T | ANGUS AND HEREFORD | |

-continued

PRKG2 SNPs

| Exon | Position | SNP | Breed | ID# |
|---|---|---|---|---|
| 16 | 237 | A/G | ANGUS | 9C40 |
| | | A/A | ANG, HER, BRAHM | 8242 |
| | | G/G | ANGUS | 257 |
| 17 | 105 | G/G | ANGUS AND HEREFORD | 257 |
| | | G/T | Angus and Brahman | 9C40 |
| | | T/T | ANGUS | 8242 |
| | 128 | C/C | ANGUS AND HEREFORD | 8242, 9C40 |
| | | C/T | BRAHMAN | |
| | 155 | C/C | ANGUS | 8242 |
| | | C/G | Angus and Brahman | 9C40 |
| | | G/G | ANGUS AND HEREFORD | 257 |
| | 410 | A/A | HEREFORD | |
| | | G/G | Angus and Brahman | |
| | 434 | A/A | ANGUS | 8242 |
| | | A/T | Angus and Brahman | 9C40 |
| | | T/T | ANGUS AND HEREFORD | 257 |
| 18 | 129 | A/C | BRAHMAN | |
| | | C/C | ANGUS | 8242 |
| | | A/A | ANGUS AND HEREFORD | 257 |
| | 159 | A/C | BRAHMAN | |
| | | C/C | ANGUS AND HEREFORD | |
| | | A/A | ANGUS | 8242 |
| | 223 | INS C | ANGUS | 8242 |
| | | C/DEL | ANGUS | 9C40 |
| | | | BRAHMAN | BR7 |
| | | DEL/DEL | ANGUS AND HEREFORD | 257 |
| | 228 | A/A | ANGUS AND HEREFORD | 257 |
| | | A/A | BRAHMAN | |
| | | T/T | ANGUS | 8242 |
| | 234 | INS GG | ANGUS | 8242 |
| | | DEL/DEL | ANGUS AND HEREFORD | 9C40, 257 |
| | | DEL/DEL | BRAHMAN | |
| | 239 | G/G | ANGUS AND HEREFORD | 257 |
| | | T/T | ANGUS | 8242 |
| | | G/T | Angus and Brahman | 9C40 |
| | 277 | T/T | ANGUS AND HEREFORD | |
| | | G/G | ANGUS | 8242 |
| | | T/G | Angus and Brahman | 9C40 |
| | 524 | A/A | ANGUS AND HEREFORD | 8242 |
| | | T/T | ANGUS | 257 |
| | | A/T | Angus and Brahman | 9C40 |
| | 558 | T/C | Angus and Brahman | 9C40 |
| | | T/T | ANGUS | 8242 |
| | | C/C | ANGUS AND HEREFORD | 257 |
| | 749 | A/G | Angus and Brahman | 9C40 |
| | | A/A | ANGUS | 8242 |
| | | G/G | ANGUS AND HEREFORD | 257 |
| | 804 | A/G | Angus and Brahman | 9C40 |

PRKG2 SNPs (continued)

| Exon | Position | SNP | Breed | ID# |
|---|---|---|---|---|
| | | A/A | ANGUS | 8242 |
| | | G/G | ANGUS AND HEREFORD | 257 |
| | 836 | A/G | Angus and Brahman | 9C40 |
| | | A/A | ANGUS AND HEREFORD | 257 |
| | | G/G | ANGUS | 8242 |
| | 920 | A/G | Angus and Brahman | 9C40 |
| | | A/A | ANGUS AND HEREFORD | 257 |
| | | G/G | ANGUS | 8242 |

BMP2K SNP

| Exon | Position | SNP | Breed | ID# |
|---|---|---|---|---|
| 5' UTR | 343 | A/G | ANGUS | 9C40 |
| | | A/A | ANGUS, HEREFORD, BRAHMAN | 8, 242, 257 |
| | 375 | A/G | ANGUS | 9C40 |
| | | A/A | BRAHMAN | |
| | | G/G | HEREFORD | |
| 1 | | | | |
| 2 | 113 | G/A | HEREFORD | |
| | 144 | G/C | BRAHMAN | |
| | 227 | A/G | BRAHMAN | |
| | 245 | C/T | BRAHMAN | |
| 3 | 5 | A/G | ANGUS | 8242 |
| | 272 | G/T | ANGUS | 8242 |
| | 435 | A/C | ANGUS | 9C40, 257 |
| | | A/A | BRAHMAN | BR7 |
| | | C/C | ANGUS AND HEREFORD | 8242, HH846 |
| 4 | NO SNP | | | |
| 5 | | | | |
| 6 | 547 | G/A | ANGUS AND BRAHMAN | 9C40, BR7 |
| 7 | 107 | G/A | BRAHMAN | |
| | 425 | T/G | ALL | |
| 8 | | | | |
| 9 | 46 | A/G | ANGUS | 9C40 |
| | 58 | G/T | ANGUS AND BRAHMAN | 257 |
| | 244 | C/A | BRAHMAN | |
| 10 | 104 | T/C | ANGUS AND HEREFORD | 8242, 9C40, 257 |
| | | T/T | BRAHMAN | |
| | 131 | A/G | ANGUS AND HEREFORD | 8242 |
| | 317 | C/G | ANGUS AND HEREFORD | 8242, 9C40, 257 |
| | | G/G | BRAHMAN | |

BMP2K SNP (continued)

| Exon | Position | SNP | Breed | ID# |
|---|---|---|---|---|
| 11 | 213 | A/T | ANGUS AND HEREFORD | 8242, 9C40, 257 |
| | | T/T | BRAHMAN | |
| | 308 | A/G | HEREFORD | |
| 12 | NO SNP | | | |
| 13 | NO SNP | | | |
| 14 | | | | |
| 15 | 179 | A/A | ANGUS AND HEREFORD | 8242, 9C40, 257 |
| | | G/G | BRAHMAN | |
| 3UTR | 479 | C/T | ANGUS | 9C40, 257 |
| | | T/T | HEREFORD | |
| | | C/C | BRAHMAN | |

BMP3 SNP

| Exon | Position | SNP | Breed | ID# |
|---|---|---|---|---|
| 5' UTR | NO SNP | | | |
| 1 | | | | |
| | 29 | A/T? | ANGUS | 257 |
| | 49 | T/G | ANGUS | 8242 |
| | 52 | A/T? | ANGUS | 8242 |
| | 194 | C/T | BRAHMAN | |
| | | C/C | ANGUS AND HEREFORD | |
| | 619 | A/T? | ANGUS | 8242 |
| | 631 | A/G | ANGUS | 8242 |
| | 644 | A/A | ANGUS AND HEREFORD | |
| | | G/G | BRAHMAN | |
| 2 | Not Available | | | |
| 3 | Not Available | | | |
| 3' UTR | 431 | a/a | ANGUS AND BRAHMAN | |
| | | g/g | HEREFORD | HH846 |

FGF5 SNPs

| Exon | Position | SNP | Breed | ID# |
|---|---|---|---|---|
| 5' UTR | Not Available | | | |
| 1 | 137 | C/G | BRAHMAN | |
| | | C/C | ANGUS | |
| | | G/G | HEREFORD | |
| 2A | 381 | A/G | BRAHMAN | BR7 |
| | 534 | G/T | BRAHMAN | BR7 |
| | | G/G | HEREFORD | HH846 |
| | | T/T | ANGUS | 9C40, 257 |
| 2C | 265 | T/G | BRAHMAN | BR7 |
| | 374 | G/C | BRAHMAN | BR7 |
| | 583 | C/T | BRAHMAN | BR7 |
| | 760 | C/T | HEREFORD | |
| | 933 | C/T | BRAHMAN | BR7 |
| 3A | 59 | A/G? | ANGUS | 257 |
| 4 | Not Available | | | |
| 5 | Not Available | | | |
| 3'UTR | Not Available | | | |

?= SNP may not be real and could not be verified by multiple sequence comparisons.

What is claimed is:

1. A method for detecting dwarfism in an Angus bovine subject, said method comprising:
   a) providing an Angus bovine genetic sample,
   b) detecting, in said genetic sample, the presence or absence of an A at position 188 of SEQ ID NO: 17, and
   c) detecting dwarfism when said Angus bovine is homozygous for A at position 188 of SEQ ID NO: 17.

2. A method of detecting carriers of a mutation that causes dwarfism in Angus bovine comprising:
   obtaining a sample of genetic material from said bovine;
   assaying for the presence of an allele characterized by a polymorphism of an A at position 188 of SEQ ID NO:17 in said sample; and
   correlating the presence of the A allele with the dwarfism trait, wherein the presence of the A allele indicates the bovine is a carrier for the dwarfism trait.

3. The method of claim 2 wherein said step of assaying is selected from the group consisting of: restriction fragment length polymorphism (RFLP) analysis, minisequencing, MALD-TOF, SINE, heteroduplex analysis, one base extension methods, single strand conformational polymorphism (SSCP), denaturing gradient gel electrophoresis (DGGE) and temperature gradient gel electrophoresis (TGGE).

4. The method of claim 2, further comprising a step of amplifying a portion of the bovine PRKG2 gene that contains said polymorphism.

5. The method of claim 4, wherein said amplification includes the steps of:
   selecting a forward and a reverse primer capable of amplifying a region of the PRKG2 gene which contains exon 15.

* * * * *